(12) United States Patent
Tacha et al.

(10) Patent No.: US 9,816,997 B2
(45) Date of Patent: Nov. 14, 2017

(54) ANTI-SOX10 ANTIBODY SYSTEMS AND METHODS

(71) Applicant: Biocare Medical, LLC, Concord, CA (US)

(72) Inventors: David Tacha, San Ramon, CA (US); Weimin Qi, Martinez, CA (US)

(73) Assignee: Biocare Medical, LLC, Concord, CA (US)

( * ) Notice: Subject to any disclaimer, the term of this patent is extended or adjusted under 35 U.S.C. 154(b) by 0 days.

(21) Appl. No.: 15/026,904

(22) PCT Filed: Oct. 3, 2014

(86) PCT No.: PCT/US2014/059162
§ 371 (c)(1),
(2) Date: Apr. 1, 2016

(87) PCT Pub. No.: WO2015/051320
PCT Pub. Date: Apr. 9, 2015

(65) Prior Publication Data
US 2016/0216269 A1 Jul. 28, 2016

Related U.S. Application Data

(60) Provisional application No. 61/886,488, filed on Oct. 3, 2013, provisional application No. 61/941,907, filed on Feb. 19, 2014.

(51) Int. Cl.
*G01N 33/574* (2006.01)
*C07K 16/18* (2006.01)
*C07K 16/30* (2006.01)

(52) U.S. Cl.
CPC ....... *G01N 33/57496* (2013.01); *C07K 16/18* (2013.01); *C07K 16/3053* (2013.01); *C07K 2317/14* (2013.01); *C07K 2317/20* (2013.01); *C07K 2317/33* (2013.01); *C07K 2317/34* (2013.01); *C07K 2317/56* (2013.01); *G01N 2333/47* (2013.01)

(58) Field of Classification Search
CPC ......... G01N 33/57496; G01N 2333/47; C07K 16/3053; C07K 16/18; C07K 2317/56; C07K 2317/34; C07K 2317/33; C07K 2317/14; C07K 2317/20
See application file for complete search history.

(56) References Cited

U.S. PATENT DOCUMENTS

| | | |
|---|---|---|
| 4,145,406 A | 3/1979 | Schick et al. |
| 4,254,082 A | 3/1981 | Schick et al. |
| 4,637,996 A * | 1/1987 | Konishi ............ C07K 5/06147 514/13.2 |
| 4,687,732 A | 8/1987 | Ward et al. |
| 4,690,890 A | 9/1987 | Loor et al. |
| 4,792,521 A | 12/1988 | Shochat |
| 4,863,875 A | 9/1989 | Bailey et al. |
| 5,089,423 A | 2/1992 | Diamiandis et al. |
| 5,108,896 A | 4/1992 | Philo et al. |
| 5,252,487 A | 10/1993 | Bacus et al. |
| 5,280,108 A | 1/1994 | Fanning |
| 5,482,698 A | 1/1996 | Griffiths |
| 5,487,975 A | 1/1996 | Miller et al. |
| 5,565,332 A | 10/1996 | Hoogenboom |
| 5,620,845 A | 4/1997 | Gould et al. |
| 5,691,154 A | 11/1997 | Callstrom et al. |
| 5,719,063 A | 2/1998 | Block |
| 5,869,274 A | 2/1999 | Tsao et al. |
| 5,891,658 A | 4/1999 | Klainer et al. |
| 6,008,057 A | 12/1999 | Glass et al. |
| 6,051,693 A | 4/2000 | Handley et al. |
| 6,252,053 B1 | 6/2001 | Ohbayashi et al. |
| 6,403,769 B1 | 6/2002 | Larochelle et al. |
| 6,409,990 B1 | 6/2002 | Vera |
| 6,476,206 B1 | 11/2002 | Sidransky et al. |
| 6,537,745 B2 | 3/2003 | Chien et al. |
| 6,580,056 B1 | 6/2003 | Tacha |
| 6,723,506 B2 | 4/2004 | Fletcher et al. |
| 6,946,256 B1 | 9/2005 | McKeon et al. |
| 7,354,584 B2 | 4/2008 | Reed |
| 7,422,739 B2 | 9/2008 | Anderson et al. |
| 7,468,425 B2 | 12/2008 | Sidransky et al. |
| 7,674,605 B2 | 3/2010 | Lin et al. |
| 7,785,803 B2 | 8/2010 | Achen et al. |
| 7,846,726 B2 | 12/2010 | Li et al. |

(Continued)

FOREIGN PATENT DOCUMENTS

| | | |
|---|---|---|
| EP | 2402370 A1 | 1/2012 |
| EP | 1733437 B1 | 9/2014 |

(Continued)

OTHER PUBLICATIONS

Tacha et al. "A Newly Developed Mouse Monoclonal SOX10 Antibody Is a Highly Sensitive and Specific Marker for Malignant Melanoma, Including Spindle Cell and Desmoplastic Melanomas" Archives of Pathology & Laboratory Medicine: Apr. 2015, vol. 139, No. 4, pp. 530-536; Epub Dec. 1, 2014; doi: http://dx.doi.org/10.5858/arpa.2014-0077-OA.*
Harlow, E. and Lane, D., Antibodies: A Laboratory Manual (1988) Cold Spring Harbor Laboratory Press, Cold Spring Harbor, NY, pp. 23-24 and 72-76.*
Van Regenmortel et al. "Molecular dissection of protein antigens and the prediction of epitopes", Chapter 1 in: Laboratory Techniques in Biochemistry and Molecular Biology vol. 19, 1988, pp. 1-39.*
Kuby et al. Immunology, W.H. Freeman and Company (1992), p. 125.*
Bost et al. "Antibodies against a peptide sequence within the HIV envelope protein crossreacts with human interleukin-2" Immunol. Invest. 1988; 17:577-586.*

(Continued)

*Primary Examiner* — Christine Foster
(74) *Attorney, Agent, or Firm* — Santangelo Law Offices, PC

(57) ABSTRACT

The present invention is related to the anti-SOX10 antibodies, kits, cocktails, and use of anti-SOX10 antibodies for detection of cancer.

14 Claims, 23 Drawing Sheets

(56) References Cited

U.S. PATENT DOCUMENTS

| | | | |
|---|---|---|---|
| 7,846,762 | B2 | 12/2010 | Rana et al. |
| 7,875,705 | B2 | 1/2011 | Iwaneri et al. |
| 7,935,794 | B2 | 5/2011 | Pullen |
| 7,935,795 | B2 | 5/2011 | Nakajima |
| 7,935,796 | B2 | 5/2011 | Lee et al. |
| 7,973,138 | B2 | 7/2011 | Liang et al. |
| 8,153,126 | B2 | 4/2012 | Violette et al. |
| 8,168,409 | B2 | 5/2012 | Calzone et al. |
| 8,338,576 | B2 | 12/2012 | Paralkar et al. |
| 8,603,765 | B2 | 12/2013 | Tacha |
| 8,852,592 | B2 | 10/2014 | Qi et al. |
| 9,005,612 | B2 | 4/2015 | Ledbetter et al. |
| 9,156,915 | B2 | 10/2015 | Waldman et al. |
| 9,417,243 | B2 | 8/2016 | Qi et al. |
| 9,428,576 | B2 | 8/2016 | Tacha et al. |
| 9,429,577 | B2 | 8/2016 | Qi et al. |
| 9,442,049 | B2 | 9/2016 | Barker et al. |
| 2002/0106685 | A1 | 8/2002 | Henning et al. |
| 2002/0173053 | A1 | 11/2002 | Damaj et al. |
| 2003/0017491 | A1 | 1/2003 | Shi et al. |
| 2005/0083802 | A1 | 4/2005 | Akahoshi et al. |
| 2005/0186642 | A1 | 8/2005 | Tacha |
| 2006/0148063 | A1 | 7/2006 | Fauzzi et al. |
| 2007/0015908 | A1 | 1/2007 | Fischer et al. |
| 2007/0041972 | A1 | 2/2007 | Rother et al. |
| 2008/0267988 | A1* | 10/2008 | Calenoff ............... C07K 7/06 424/185.1 |
| 2009/0191190 | A1 | 7/2009 | Barghorn et al. |
| 2010/0047825 | A1 | 2/2010 | Tacha |
| 2010/0092457 | A1 | 4/2010 | Aburatani et al. |
| 2012/0082999 | A1 | 4/2012 | Liao et al. |
| 2012/0154983 | A1 | 6/2012 | Zhang et al. |
| 2012/0245051 | A1 | 9/2012 | Rimm et al. |
| 2012/0321557 | A1 | 12/2012 | Kimura |
| 2014/0004542 | A1 | 1/2014 | Qi et al. |
| 2014/0057803 | A1 | 2/2014 | Tacha |
| 2015/0056635 | A1 | 2/2015 | Qi et al. |
| 2015/0152180 | A1 | 6/2015 | Davis et al. |
| 2016/0009795 | A1 | 1/2016 | Tacha et al. |
| 2016/0333085 | A1 | 11/2016 | Tacha |
| 2016/0334407 | A1 | 11/2016 | Qi et al. |
| 2016/0370370 | A1 | 12/2016 | Qi et al. |

FOREIGN PATENT DOCUMENTS

| | | |
|---|---|---|
| WO | 99/50287 A2 | 10/1999 |
| WO | 03003906 A2 | 1/2003 |
| WO | 2005054860 A1 | 6/2005 |
| WO | 2005076005 A2 | 8/2005 |
| WO | 2005083802 A1 | 9/2005 |
| WO | 2010022736 A2 | 3/2010 |
| WO | 2010124689 A1 | 11/2010 |
| WO | 2012031273 A2 | 3/2012 |
| WO | 2012154983 A2 | 11/2012 |
| WO | 2012154983 A3 | 11/2012 |
| WO | 2014052672 A1 | 4/2014 |
| WO | 2014100220 A2 | 6/2014 |
| WO | 2014134587 A1 | 9/2014 |
| WO | 2015051320 A2 | 4/2015 |
| WO | 2015051320 A2 | 8/2016 |

OTHER PUBLICATIONS

Bendayan, M. "Possibilities of false immunocytochemical results generated by the use of monoclonal antibodies: the example of the anti-proinsulin antibody" J. Histochem. Cytochem. 1995; 43:881-886.*
European Patent App. No. 13841542.7. Extended European search report dated Apr. 28, 2016. 9 pages.
Saeb, Parsy, et al. 'Diagnosis of Bladder Cancer by Immunocytochemical detection of minichromosome maintenance protein-2 in cells retrieved from urine' British Journal of Cancer (2012) 107, 1384-1391.
Nonaka, D. et al. Diagnostic Utility of Thyroid Transcription factors PAX8 and TTF-2 in Thyroid Epithelial Neoplasms. Mod Pathol. Feb. 2008; 21(2): 192-2004.
International Application No. PCT/US13/62043, entitled Anti-Uroplakin II Antibodies Systems and Methods, filed Sep. 26, 2013, Search Report, dated Jan. 29, 2014. 6 pages.
International Application No. PCT/US13/62043, entitled Anti-Uroplakin II Antibodies Systems and Methods, filed Sep. 26, 2013, Written Opinion, dated Jan. 29, 2014. 22 pages.
International Application No. PCT/US14/59162; filed Oct. 3, 2014. International Preliminary Report on Patentability, 6 pages. dated Apr. 5, 2016.
Chames et al. Therapeutic antibodies: success, limitations and hopes for the future. Themed Section: Vector Design and Drug Delivery Review. British Journal of Pharmacology (2009) 157,200-233.
Jakobovits, Aya. Production of fully human antibodies by transgenic mice. Cell Genesys Inc., Foster City, USA. Current Opinion in Biotechnology, 1995, 6:561-566.
Kellermann & Green, Antibody discovery: the use of transgenic mice to generate human monoclonal antibodies for therapeutics. Current Opinion in Biotechnology, 2002, 13:593-597.
Morrison et al. Chimeric human antibody molecules: Mouse antigen-binding domains with human constant region domains. Proc. Natl. Adad. Sci. USA. vol. 81, pp. 6851-6855, Nov. 1984.
Winter et al. Humanized antibodies. Immunology Today vol. 14 No. 6, 1993. 4 pages.
Bostwick, DG and Qian, J., Mod. Pathol., 2004, 17, 360, "High-grade prostatic intraepithelial neoplasia" (20 pages total).
Herawi, M and Epstein, JI, Am. J. Surg. Path., 2007, 31, 889, "Immunohistochemical antibody cocktail staining (p63/HMWCK/AMACR) of ductal adenocarcinoma and Gleason pattern 4 cribriform and noncribriform acinar adenocarcinomas of the prostate" (6 pgs total).
Jiang, Z et. al., Am. J. Clin. Path., 2004, 122, 275, "Discovery and clinical application of a novel prostate cancer marker: alpha-methylacyl CoA racemase (P5043)" (15 pages total).
Jiang, Z et. al., Am. J. Clin. Path., 2005, 123,231, "Using an AMACR (P504S)/34betaE12/p63 cocktail for the detection of small focal prostate carcinoma in needle biopsy specimens" (6 pages total).
Jiang, Z et. al., Am. J. Surg. Path., 2001, 25, 1397, "P504S: a new molecular marker for the detection of prostate carcinoma" (8 pages total).
Luo, J et. al., Cancer. Res., 2002, 62, 2220, "Alpha-methylacyl-CoA racemase: a new molecular marker for prostate cancer" (7 pages total).
Reis-Filho et al, Virchows Arch. (2003) vol. 443, pp. 122-132.
12 pages from catalog: "product information form the Sigma-Aldrich Online Catalog" at sigmaaldrich.com/ .. ./ProductDetail.do?I . . . accessed Feb. 14, 2011, Product No. A574, 3-Amino-9-ethylcarbazole.
8 pages from catalog: "product information form the Sigma-Aldrich Online Catalog" at sigmaaldrich.com/ .. ./ProductDetail.do?I . . . accessed Feb. 16, 2011, Catalog No. F1505, "Fast Red KB Salt".
Epstein, JI, and Netto, GJ., Biopsy interpretation of the prostate, 2008, Lippincott, Williams & Wilkins: Philadelphia, p. 99.
BioSB p40 IHC of p40 on an FFPE Prostate Tissue, http://www.biosb.com/p40-page, Jul. 29, 2015, 4 pages.
Zeta Corporation IVD Data Sheet (Rev 052014) p40 (Clone ZR8), 7 pages. Dated Jun. 24, 2015.
U.S. Appl. No. 61/770,956 entitled "Systems and Methods for Anti-p40 Antibodies" filed Feb. 28, 2013, (50 pages total).
European Patent App. No. 14178215.1 Examination Report dated Dec. 15, 2015, 5 pages.
European Patent App. No. 14178215.1 Search Report dated Dec. 1, 2014, 11 pages.
Laury A.R. et al. A comprehensive analysis of PAX8 expression in human epithelial tumors. Am J Surg Pathol 2011;35:816-826.
Moretti L. et al. N-terminal PAX8 polyclonal antibody shows cross-reactivity with N-terminal region of PAX5 and is responsible for reports of PAX8 positivity in malignant lymphomas. Mod Pathol 2011.
Long K. B. et al. PAX8 Expression in well-differentiated pancreatic endocrine tumors: correlation with clinicopathologic features and

(56) References Cited

OTHER PUBLICATIONS comparison with gastrointestinal and pulmonary carcinoid tumors. Am J Surg Pathol 2010;34:723-729.
Haynes C. M. et al. PAX8 is expressed in pancreatic well-differentiated neuroendocrine tumors and in extrapancreatic poorly differentiated neuroendocrine carcinomas in fine-needle aspiration biopsy specimens. Cancer Cytopathol 2011;119:193-201.
Sangoi A. R. et al. PAX8 expression reliably distinguishes pancreatic well-differentiated neuroendocrine tumors from ileal and pulmonary well-differentiated neuroendocrine tumors and pancreatic acinar cell carcinoma. Mod Pathol 2011;24:412-424.
Lorenzo P.I. et al. Immunohistochemical assessment of Pax8 expression during pancreatic islet development and in human neuroendocrine tumors. Histochem Cell Biol 2011;136:595-607.
Ye J. et al. Diagnostic utility of PAX8, TTF-1 and napsin A for discriminating metastatic carcinoma from primary adenocarcinoma of the lung. Biotech Histochem 2011.
Albadine R. et al. PAX8 (+)/p63 (−) immunostaining pattern in renal collecting duct carcinoma (CDC): a useful immunoprofile in the differential diagnosis of CDC versus urothelial carcinoma of upper urinary tract. Am J Surg Pathol 2010;34:965-969.
Laury A.R. et al. PAX8 reliably distinguishes ovarian serous tumors from malignant mesothelioma. Am J Surg Pathol 2010;34:627-635.
Turque N. et al. Pax-QNR/Pax-6, a paired box- and homeobox-containing gene expressed in neurons, is also expressed in pancreatic endocrine cells. Mol Endocrinol 1994;8:929-938.
U.S. Appl. No. 61/588,035, filed Jan. 18, 2012, Entitled Anti-PAX8 Antibodies Systems and Methods.
Tockman et al, Consideration in Bringing a Cancer Biomarker to Clinical Application. Cancer Research vol. 52 p. 2711s (1992), (8 pages total).
Janicke et al., Urokinase-type Plasminogen Activator (u-PA) Antigen in a Predictor of Early Relapse in Breast Cancer. Fibrinolysis vol. 4 p. 69 (1990).
Paul, Structure and Function of Immunoglobulins. Fundemental Immunology, 3rd Edition, 1993, pp. 292-295.
Rudikoff et al Single Amino Acid Substitution Altering Antigen-binding Specificity (Proc. Natl. Acad. Sci. USA 1982 vol. 79: p. 1979-82).
de Pascalis et al., Grafting of "Abbreviated" Complementarity-Determining Regions Containing Specificity-Determining Residues Essential for Ligand Contact to Engineer a Less Immunogenic Humanized Monoclonal Anitbody. (The Journal of Immunology (2002) 169,3076-3084).
Brown et al. Tolerance to Single, but Not Multiple, Amino Acid Replacements in Anitbody VH CDR2. (J. Immunol. May 1996; 156(9):3285-3291.
Casset et al. A Peptide Mimetic of an Anti-CD4 Monoclonal Antibody by Rational Design. (2003) BBRC 307, 198-205.
Brown, H. M. et al. Uroplakin-III to Distinguish Primary Vulvar Paget Disease From Paget Disease Secondary to Urothelial Carcinoma, Human Path. 2002;33:545-548.
Koga, F. et al. Impaired p63 Expression Associates with Poor Prognosis and Uroplakin III Expression in Invasive Urothelial Carcinoma of the Bladder, Clin Cancer Res. 2003;9:5501-5507.
Logani, S. et al. Immunoprofile of Ovarian Tumors With Putative Transitional Cell (Urothelial) Differentiation Using Novel Urothelial MarkersHistogenetic and Diagnostic Implications, Am J Surg Pathol 2003;27:1434-1441.
Matsumoto, K. et al. Loss Expression of Uroplakin III is Associated with Clinicopathologic Features of Aggressive Bladder Cancer, Urology. 2008;72:444-449.
Mhawech, P. et al. Immunohistochemical Profile of High-Grade Urothelial Bladder Carcinoma and Prostate Adenocarcinoma, Human Path. 2002;33:1136-1140.
Ogawa, K. et al. Immunohistochemical Analysis of Uroplakins, Urothelial Specific Proteins, in Ovarian Brenner Tumors, Normal Tissues, and Benign and Neoplastic Lesions of the Female Genital Tract. Am J Pathol. 1999;155:1047-1050.
Ohtsuka, Y. et al. Loss of uroplakin III expression is associated with a poor prognosis in patients with urothelial carcinoma of the upper urinary tract, BJU International, 2006;97:1322-1326.
Parker, D. C. et. al. Potential Utility of Uroplakin III, Thrombomodulin, High Molecular Weight Cytokeratin, and Cytokeratin 20 in Noninvasive, Invasive, and Metastatic Urothelial (Transitional Cell) Carcinomas, Am J Surg Pathol 2003;27:1-10.
Wu, X. R. et. al. Mammalian Uroplakins, A group of highly conserved urothelial differentiation-related membrane proteins, J Biol Chem. 1994;269:13716-13724.
Moll, R. et al. Uroplakins, Specific Membrane Proteins of Urothelial Umbrella Cells, as Histological Markers of Metastatic Transitional Call Carcinomas. Am J Pathol, vol. 147, No. 5, Nov. 1995.
Kaufmann, O. et al. Uroplakin III Is a Highly Specific and Moderately Sensitive Immunohistochemical Marker for Primary and Metastatic Urothelial Carcinomas, Am J Clin Pathol 2000;113:683-687.
Wu, RL et al. Uroplakin II Gene is expressed in transitional cell carcinoma but not in bilharzial bladder squamous cell carcinoma: alternative pathways of bladder epithelial differentiation and tumor formation. Cancer Research, Mar. 15, 1998, vol. 58, No. 6, pp. 1291-1297.
Yu, C et al. PSA and NIKX3.1: A Comparative IHC Study of Sensitive and Specificity in Prostate Cancer. BioCareMedical, Presented at USCAP, Abstract #1070, Mar. 19-21, 2012. <uri: http://biocare.net/wp-content/uploads/PSANKX100.pdf>, (four pages total).
Wu XR, Kong XP, Pellicer A, Kreibich G, Sun TT.; Uroplakins in urothelial biology, function, and disease; Kidney Int. Jun. 2009;75(11):1153-65.
Wu X, Kakehi Y, Zeng Y, Taoka R, Tsunemori H, Inui M. J ; Uroplakin II as a promising marker for molecular diagnosis of nodal metastases from bladder cancer: comparison with cytokeratin 20.; Urol. Dec. 2005;174(6):2138-4.
Olsburgh J, Harnden P, Weeks R, Smith B, Joyce A, Hall G, Poulsom R, Selby P, Southgate J.J; Uroplakin gene expression in normal human tissues and locally advanced bladder cancer Pathol. Jan. 2003;199(1):41-9.
Lu JJ, Kakehi Y, Takahashi T, Wu XX, Yuasa T, Yoshiki T, Okada Y, Terachi T, Ogawa O; Detection of circulating cancer cells by reverse transcription-polymerase chain reaction for uroplakin II in peripheral blood of patients with urothelial cancer; Clin Cancer Res. Aug. 2000;6(8):3166-71.
Li, S.M., et al. Detection of circulating uroplakin-positive cells in patients with transitional cell carcinoma of the bladder; J Urol. Sep. 1999;162(3 Pt 1):931-5.
Kong XT, Deng FM, Hu P, Liang FX, Zhou G, Auerbach AB, Genieser N, Nelson PK, Robbins ES, Shapiro E, Kachar B, Sun TT.; Roles of uroplakins in plaque formation, umbrella cell enlargement, and urinary tract diseases. J Cell Biol. Dec. 20, 2004;167(6):1195-204.
Okegawa T, Kinjo M, Nutahara K, Higashihara E.; Value of reverse transcription polymerase chain assay in peripheral blood of patients with urothelial cancer. J Urol. Apr. 2004;171(4):1461-6.
Hong-Ying Huang, Shahrokh F. Shariat, Tung-Tien Sun, Herbert Lepor, Ellen Shapiro, Jer-Tsong Hsieh, Raheela Ashfaq, Yair Lotan, and Xue-Ru Wu, ; Persistent Uroplakin Expression in Advanced Urothelial Carcinomas: Implications in Urothelial Tumor Progression and Clinical Outcome. Hum Pathol. Nov. 2007; 38(11): 1703-1713.
Lai, Y. et al. UPK3A: A promising novel urinary marker for the detection of bladder cancer, Urology 76(2), 2010.
Tacha et al. 'A 6-Anitbody Panel for the Classification of Lung Adenocarcinoma Versus Squamous Cell Carcinoma.' Appl Immunohistochem Mol Morphol. 20(3): 201-7, May 2012.
Baty et al. 'Gene profiling of Icinical routine biopsies and prefiction of survival in non-small cell lung cancer.' Am J Respir Crit Care Med. 181(2):181-8.Oct. 15, 2009, (61 pages total).
Brown, et al. 'Tissue Preserving Antibody Cocktails to Differentiate Primary Squamous Cell Carcinoma, Adenocarcinoma, and Small Cell Carcinoma of Lung.' Arch Pathol Lab Med. 137(9):1274-81. Jan. 4, 2013.

(56) References Cited

OTHER PUBLICATIONS

Whithaus K., et al. Evaluation of Napsin A, Cytokeratin 5/6, p63, and Thyroid Transcription Factor 1 in Adenocarcioma Versus Squamous Cell Carcinoma of Lung. Arch Pathol Lab Med. 2012; 136: 155-162.
Savci-Heijink C. D., et al. The role of desmoglein-3 in the diagnosis of squamous cell carcinoma of the lung. Am J Pathol. 2009;174(5): 1629-1637.
Ring B. Z., et al. A novel five-antibody immunohisto-chemical test for subclassification of lung carcinoma. Mod Pathol. 2009;22(8): 1032-1043.
Mukhopadhyay S., et al. Subclassification of Non-small Cell Lung Carcinomas lacking Morphologic Differentiation on biopsy specimens: Utility of an Immunohistochemical Panel Containing TTF-1, Napsin A, p63 and CK 5/6. Am J Surg Pathol, 2011; 35(1): 15-25.
Bishop J. A., p40 (ΔNp63) is superior to p63 for the diagnosis of pulmonary squamous cell carcinoma, Modern Pathology (2011), 1-11; republished Mar. 2012;25(3):405-15.
Ikeda S, et al. "Combined immunohistochemistry of beta-catenin, cytokeratin 7, and cytokeratin 20 is useful in discriminating primary lung adenocarcinomas from metastatic colorectal cancer.", BMC Cancer. Feb. 2, 2006;6:31, (6 pages total).
Chopra, N. et al. 'Inducing Protectice Antibodies Against Ring-Infected Erythrocyte Surface Peptide Antigen of Plasmodium Falciparum Using Immunostimulating Complex (Iscoms) Delivery.' Med Microbiol. Immunol. Nov. 2000 vol. 189, No. 2: pp. 75-83.
Calbiochem-Novabiochem International. P40(Ab-1) Cat# PC373 [datasheet]. USA 2000; 2 pages, Oncogene Research Products.
Abcam. Understanding Secondary Antibodies: Fragment Antigen Binding Antibodies and Isotopes. USA 2012; 12 pages.
Biocare Medical. MACH 2 Double-Stain 2 [datasheet]. USA Mar. 2, 2011; 2 pages.
Yamaguchi, K. et al. Circulating Antibodies to P40AIS in the Sera of Respiratory Tract Cancer Patients. Int. J. Cancer. Nov. 20, 2000. vol. 89 No. 6; 5 pages.
Vaidyanathan, P. Aperio-Definins Digital Pathology Solutions [Presentation]. Jul. 7, 2011. Aperio Webinar. <http://www.aperio.com/sites/default/files/events/070611_Spectrum_Plus_ppt_for_webinar_on_integration.pd>; 10 pages.
Jain, et al. Atypical ductal hyperplasia: interobserver and intraobserver variability. Mod. Pathol. (2011) 24, 917-923.
Tacha, et al. "An Immunohitochemical Analysis of a Newly Developed Mouse Monocloncal p40 (BC28) in Lung, Bladder, Skin, Breast, Prostate, and Head and Neck Cancers" 2014 College of American Pathologists, Early Online Release, Arch Pathol. Lab Med. 8 pages, postes Feb. 2014.
Barbareschi, et al. p63, a p53 homologue, is a selective nuclear marker of myoepithelial cells of the human breast. Am J Surg. Pathol 25(8): 1054-1060,Aug. 2001.
Bergholz, et al. 'Role of p63 in development, tumorigenesis and cancer progression'. Cancer Microenvironment (2012) 5:311-322.
Di Como, et al. 'p63 Expression Profiles in Human Normal and Tumor Tissues'. Clinical Cancer Research. vol. 8, 494-501, Feb. 2002.
Hibi, et al. 'AIS is an oncogene amplified in squamous cell carcinoma'. Pro Natl Acad Sci U.S.A, May 9, 2000, vol. 97, No. 10, 5462-5467.
Kaghdad, et al. Monoallelically Expressed Gene Related to p53 a 1p36, a Region Frequently Deleted in Neuroblastoma and Other Human Cancers. Cell, vol. 90(4), 809-819, Aug. 22, 1997.
Karni-Schmidt, et al. Distinct Expression Profiles of p63 Variants during Urothelial Development and Bladder Cancer Progression. Am J Pathol vol. 178, No. 3, Mar. 2011, 1350-60.
Khoury, et al. "p53 Isoforms: An Intracellular Microprocessor?" Genes & Cancer, 2(4), 2011, 453-465.
Murray-Zmijewski, et al. p53/p63/p73 isoforms: an orchestra of isoforms to harmonise cell differentiation and response to stress. Cell Death and Differentiation (Jun. 2006); 13(6), 962-972.

Nobre, et al. 'p40: A p63 isoform useful for lung cancer diagnosis—a Review of the Physiological and Pathological Role of p63'. Acta Cytologica 2012; 57(1):1-8.
Nonaka, 'A study of Np63 expression in lung non-small cell carcinomas'. Am J Surg Pathol vol. 36 No. 6 Jun. 2012 895-9.
Nylander, et al. 'Differential expression of p63 isoforms in normal tissues and neoplastic cells'. J Pathol 2002; 198: 417-427.
Osada, et al. Cloning and functional analysis of human p51, which structurally and functinoally resembles p53, Nat Med. Jul. 1998; 4(7): 839-43.
Pelosi, et al. 'Np63 (p40) and Thyroid Transcription Factor-1 Immunoreactivity on small biopsies or cellblocks for typing non-small cell lung cancer'. Journal and Thoracic Oncology, vol. 7(2), No. 2, Feb. 2012, 281-90.
Senoo et al. 'A second p53-Related Protein, p73L, with High Homology to p73'. Biophys Res Commun. Jul. 30, 1998; 248(3), 603-607.
Trink, et al. A new human p53 homologue, Nat Med. Jul. 1998; 4(7): 747-8.
Yang, et al. 'p63, a p53 homolog at 3q27-29, encodes multiple products with transactivating, death-inducing, and dominant-negative activities'. Molecular Cell, vol. 2(3), 305-316, Sep. 1998.
Bowen, et al. 'Emerging roles for PAX8 in ovarian cancer and endosalpingeal development.' Gynecologic Oncology, vol. 104, No. 2, Feb. 2007, 331-337.
Tacha, D. et al. Expression of PAX8 in Normal and Neoplastic Tissues: A Comprehensive Immunohistochemical Study. Appl. Immun. Mol. Morph. 2011, pp. 293-299.
Kobel M. et al. Ovarian carcinoma subtypes are different diseases: Implications for biomarker studies. PLoS Med. Dec. 2, 2008; 5(12): e232.
Nonaka D. et al. Expression of PAX8 as useful marker in distinguishing ovarian carcinomas from mammary carcinomas. Am J Surg Pathol. Oct. 2008; 32(10):1566-71.
Tong G. X. et al. Expression of PAX8 in nephrogenic adenoma and clear cell adenocarcinoma of the lower urinary tract: evidence of related histogenesis? Am J Surg Pathol. Sep. 2008; 32(9):1380-7.
Tong G. X. et al. Expression of PAX8 in normal and neoplastic renal tissues: an immunohistochemical study. Mod. Pathol. Sep. 2009; 22 (9):1218-27.
Mazal P. R. et al. Expression of aquaporins and PAX-2 compared to CD10 and cytokeratin 7 in renal neoplasms: a tissue microarray study. Mod. Pathol. Apr. 2005; 18(4):535-40.
Avery A. K. et al. Use of antibodies to RCC and CD10 in the differential diagnosis of renal neoplasms. Am J Surg Pathol. Feb. 2000; 24(2):203-10.
Zhou M. et al. The usefulness of immunohistochemical markers in the differential diagnosis of renal neoplasms. Clin Lab Med. Jun. 2005; 25(2):247-257.
Kuehn A. et al. Expression analysis of kidney-specific cadherin in a wide spectrum of traditional and newly recognized renal epithelial neoplasms: diagnostic and histogenetic implications. Am J Surg Pathol. Oct. 2007; 31(10):1528-33.
Mazal P. R. et al. Expression of kidney-specific cadherin distinguishes chromophobe renal cell carcinoma from renal oncocytoma. Hum Pathol. Jan. 2005; 36(1):22-8.
Zhu W. et al. WT1, monoclonal CEA, TTF1, and CA125 antibodies in the differential diagnosis of lung, breast, and ovarian adenocarcinomas in serous effusions. Diag Cytopathol. Jun. 2007; 35(6):370-5.
Tornos C. et al. Expression of WT1, CA 125, and GCDFP-15 as useful markers in the differential diagnosis of primary ovarian carcinomas versus metastatic breast cancer to the ovary. Am J Surg Pathol. Nov. 2005; 29(11):1482-9.
Lee A. H. et al. The expression of Wilms' tumour-1 and CA125 in invasive micropapillary carcinoma of the breast. Histopathology. Dec. 2007; 51(6):824-8.
Reid-Nicholson M. et al. Immunophenotypic diversity of endometrial adenocarcinomas: implications for differential diagnosis. Mod Pathol. Aug. 2006; 19(8):1091-100.
Zhang P. et al. Immunohistochemical analysis of thyroid-specific transcription factors in thyroid tumors. Pathol Int 2006;56:240-245.

(56) References Cited

OTHER PUBLICATIONS

Cartron, et al. Therapeutic activity of humanized anti-DC20 monoclonal antibody and polymorphism in IgG Fc receptor gene. www.bloodjournal.org, Jan. 21, 2016. 6 pages.
Creative Biolabs, Chimeric IgG construction; (c) 2007-2016 Creative Biolabs, 2 pages.
Foran, James M. et al. European Phase II Study of Rituximab (Chimeric Anti-CD20 Monoclonal Antibody) for Patients with Newly Diagnosed Mantle-Cell Lymphoma and Previously Treated Mantle-Cell Lymphoma, Immunocytoma, and Small B-Cell Lymphocytic Lymphoma. Journal of Clinical Oncology, vol. 18, No. 2/317; Jan. 1, 2000, 7 pages, Abstract Only.
Eng, Hui-Yan, et al. Enhanced antigen detection in immunohistochemical staining using a 'digitized' chimeric antibody. Oxford, Protein Engineering, Design & Selection, 2016, vol. 29 No. 1, pp. 11-21. Sep. 25, 2015, 11 pages.
Carter, Paul J. Potent antibody therapeutics by design. Nature Reviews, Immunology. vol. 6, May 2006. pp. 343-357. 15 pages.
Panka et al. Variable region framework differences result in decreased or increased affinity of variant anti-digoxin antibodies. Proc. Natl. Acad. Sci. USA, vol. 85, pp. 3080-3084, May 1988.
Harris et al. Assessing Genetic Heterogeneity in Production Cell Lines: Detection by Peptide Mapping of a Low Tyr to Gln Sequence Variant in a Recombinant Antibody. Biotechnology, vol. 11 p. 1293-1297, Nov. 1993.
Okazaki et al. Hydronephrosis associated with antiurothelial and antinuclear autoantibodies in BALB/ c-Fcgr2b-/-Pdcd1-/-mice. The Journal of Experimental Medicine. vol. 202, No. 12, pp. 1643-1648, Dec. 19, 2005.
International Application No. PCT/US14/59162, entitled Anti-SOX10 Antibody Systems and Methods, filed Oct. 3, 2014, Search Report, dated Apr. 13, 2015. 4 pages.
International Application No. PCT/US14/59162, entitled Anti-SOX10 Antibody Systems and Methods, filed Oct. 3, 2014, Written Opinion dated Apr. 13, 2015. 8 pages.
Bondurand, et al. The role of SOX10 during enteric nervous system development. Dev Bioi. Epub May 2, 2013, 382 (1):330-43.
GenBank Accession No. CAG30470. SOX10 (*Homo sapiens*]. Oct. 16, 2008. (Retrieved from the Internet Dec. 4, 2014: <http://www.ncbi.nlm.nih.gov/protein/CAG30470.1>] 2 pages.
International Application No. PCT/US13/76203, entitled Antibody Cocktail Systems and Methods for Classification of Histological Subtypes in Lung Cancer, filed Dec. 18, 2013, Search Report, dated Jul. 8, 2014. 6 pages.
International Application No. PCT/US13/76203, entitled Antibody Cocktail Systems and Methods for Classification of Histological Subtypes in Lung Cancer, filed Dec. 18, 2013, Written Opinion, dated Jul. 8, 2014. 10 pages.
U.S. Appl. No. 61/738,938 entititled "Systems and Methods for Antibody Cocktails for Classification of Histologic Subtypes in Lung Cancer" filed Dec. 18, 2012, (49 pages total).
International Application No. PCT/US14/19705, entitled Anti-p40 Antibodies Systems and Methods, filed Feb. 28, 2014, Search Report, dated May 23, 2014. 7 pages.
International Application No. PCT/US14/19705, entitled Anti-p40 Antibodies Systems and Methods, filed Feb. 28, 2014, Written Opinion, dated May 23, 2014. 27 pages.
Sanderson, SO et. al., "An Analysis of the p63/α-Methylacyl Coenzyme A Racemase Immunohistochemical Cocktail Stain in Prostrate Needs Biopsy Speciments and Tissue Microarrays", Am. J. Clin. Path., 2004; 121:220-225.
Zhou, Ming. al., "Basal Cell Cocktail (34βE12+p63) Improves the Detection of Prostate Basal Cells", Am. J. Surg. Path., 2003: 27(3), 365-371.
Zhou, Ming et al., "Expression and Disgnostic Utility of Alpha-Methylacyl-CoA-Racemase (P504S) in Foamy Gland and Pseudohyperplastic Prostate Cancer", Am. J. Surgical Pathology 27(6): 772-778, 2003.

Anonymous: "PIN cocktail-2 (P504S+p63)", Biocarta. May 4, 2003, pp. 1-2. XP 002667408, Retrieved from the Internet: URL:http://www.biocarta.com/TDS/PM205DSH.pdf [retrieved on Jan. 18, 2012].
Susan Van Noorden., "Immunocytochemistry for light microscopy a technical update", The biomedical Scientist, XP-002522654, Aug. 2003, pp. 808-811.
Rami Suzuki. et al., "Proliferation and differentiation in the human breast during pregnancy", Differentiation. vol. 66, No. 2-3, XP-002522647, Oct. 2000, pp. 106-115.
DAKO datasheet, DuoFlex Cocktail, Code IC004 (119877-001), Jan. 2013, 17 pages total.
Van der Loos, "Immunoenzyme Multiple Staining Methods", Microscopy Handbooks 45, (1999); Bios Scientific Publishers Ltd: Oxford, UK, (123 pages total).
Hiromichi Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, XP-002522648, May 2000, pp. 653-662.
Brunangelo Falin!, et al., "Double Labeled-Antigen Method for Demonstration of Intracellular Antigens in Paraffin-embedded Tissues", The Journal of Histochemistry and Cytochemistry. vol. 30, No. 1, pp. 21-26 (1982).
Data Sheet Fast Red Stubsrate Pack and Compponents for Use with Alakline Phosphatase Detection Kits & BioGenex Automated Staining Systems (Doc. No. HK180, Rev. No. F112) Jul. 1, 2003 accessed from web.archive.org/web/20030701115828/http://www.bioQenex.com/biOQenex h.html, (2 pages total).
Vector Red Alkaline Phosphatase Substrate Kit I Cat. No. SK-5100, Oct. 31, 2000, accessed from web.archive.org/web/20031202200453/http://www.vector.labs.com/protocols.asp, (5 pages total).
Cordell et al, Journal of Histochemistry and Cytochemistry, 1984, vol. 32, No. 2 pp. 219-229 attached online version htte://jhc.sageeub.com/content/32/2/219.
Instructions for Universal Alkaline Phosphatase Immunostaining Kit (For Mouse and Rabbit Primary Antibodies) Cat. #KA-50F Apr. 7, 2003 Accessed from web.archive.org/web/20030407222427/http:I/dbiosys.com/new/index.asp?fuse=dsp cat&id=5, (6 pages total).
Elias, Immunohistopathology—A Practical Approach to Diagnosis, 2nd Ed. , American Society for Clinical Pathology Press: Chicago, © 2003, p. 36.
Molinie, V. et. al., Mod. Pathol., 2004, 17, 1180, "Diagnostic utility of a p63/alpha-methyl-CoA-racemase (p504s) cocktail in atypical foci in the prostate".
Paner, GP, . et. al., Best Prac. In Diag. Immunohist.: Prostate, 2008, 132, 1388, (9 pages total).
Rubin, MA et. al., JAMA, 2002,287, 1662, "alpha-Methylacyl coenzyme A racemase as a tissue biomarker for prostate cancer" (9 pages total).
Shah, RB et. al., Am. J. Surg. Path., 2002, 26, 1161, "Comparison of the basal cell-specific markers, 34betaE12 and p63, in the diagnosis of prostate cancer" (8 pages total).
Signoretti, Sabina 'p63 is a prostate basal cell marker and is required for prostate development'. Am J Pathol, vol. 157, No. 6, Dec. 2000, 1769-75.
Tacha, DE and Miller, RT, Appl. Immunohistochem. Mol. Morph . . . 2004, 12, 75, "Use of p63/P504S monoclonal antibody cocktail in immunohistochemical staining of prostate tissue" (4 pages total).
Tavora. F and Epstein, JI, Am. J. Surg. Path., 2008, 32, 1060, "High-grade prostatic intraepithelial neoplasialike ductal adenocarcinoma of the prostate: a clinicopathologic study of 28 cases" (8 pages total).
Yang, Yet. al., Am. J. Path., 1997, 150, 693, "Differential expression of cytokeratin mRNA and protein in normal prostate, prostatic intraepithelial neoplasia, and invasive carcinoma" (7 pgs total).
Abrahams, NA, et. a f., Histopathology, 2002, 41, 35, "Validation of cytokeratin 5/6 as an effective substitute for keratin 903 in the differentiation of benign from malignant glands in prostate needle biopsies" (7 pages total).

(56) References Cited

OTHER PUBLICATIONS

Adley, BP et. al., Am. J. Clin. Path., 2006, 126, 849, "Alpha-methylacyl coenzyme A racemase immunoreactivity in partial atrophy of the prostate" (7 pages total).

Beach, R et. al., Am. J. Surg. Path., 2002, 26, 1588, "P504S immunohistochemical detection in 405 prostatic specimens including 376 18-gauge needle biopsies" (9 pages total).

Ozcan A. et al. PAX 8 expression in non-neoplastic tissues, primary tumors, and metastatic tumors: a comprehensive immunohistochemical study. Mod Pathol 2011;24:751-764.

Foran, James M. et al. European Phase II Study of Rituximab (Chimeric Anti-CD20 Monoclonal Antibody) for Patients with Newly Diagnosed Mantle-Cell Lymphoma and Previously Treated Mantle-Cell Lymphoma, Immunocytoma, and Small B-Cell Lymphocytic Lymphoma. Journal of Clinical Oncology, vol. 18, No. 2/317; Jan. 1, 2000, 7 pages. Abstract only.

* cited by examiner

ANTI-SOX10 ANTIBODY SYSTEMS AND METHODS

This application is the United States National Phase of International Patent Application Number PCT/US2014/059162 filed Oct. 3, 2014 which claims priority to and the benefit of U.S. Provisional Application No. 61/886,488 filed Oct. 3, 2013 and U.S. Provisional Application No. 61/941,907 filed Feb. 19, 2014, each application hereby incorporated by reference herein in its entirety.

TECHNICAL FIELD

This invention relates to the novel anti-SOX10 antibodies, compositions, cocktails, and kits comprising the antibodies and methods for using the antibodies.

BACKGROUND OF THE INVENTION

Microscopic examination of tissue samples, particularly those obtained by biopsy, is a common method for diagnosis of disease. In particular, immunohistochemistry (IHC), a technique in which specific antibodies are used to detect expression of specific proteins in the tissue sample, may be a valuable tool for diagnosis, particularly for the detection and diagnosis of cancer.

The Sry-related HMG-Box gene 10, perhaps located at chromosome 22q13, may encode a protein known as SOX 10, which is perhaps a transcription factor in humans that may be important for neural crest, peripheral nervous system, and melanocytic cell development. SOX10 may be essential for the formation of nerves in the large intestine and melanocytes. Melanocytes are perhaps cells that produce pigment, found in the skin, eyes, and hair. The SOX10 protein may be widely expressed in human normal tissues including melanocytes, breast tissue, cranial ganglia, dorsal root ganglia, and the optic vesicle. SOX10 may perhaps also be an important marker in malignant tumors such as melanoma, breast carcinoma, gliomas, and the like, as well as benign tumors such as schwannomas, and the like. The transcriptional factor SOX10 may be one of the key determinants of oligodendroglial differentiation. The majority of oligodendrogliomas, but also a large fraction of astrocytomas, including the least differentiated glioblastomas, perhaps express SOX10.

Desmoplastic melanoma may be a rare variant of invasive cutaneous melanoma, with an annual incidence rate of perhaps approximately 2 per 1,000,000. Features unique to this melanoma type may include deep invasion, increased peri-neural invasion, local recurrence and perhaps delayed diagnosis. Studies may have shown that SOX10 is a highly sensitive and specific marker of melanoma in both primary and metastatic lesions. On the basis of the expression in melanocytes of non-neoplastic and benign skin, and in benign and dysplastic nevi, SOX10 may not be a useful marker to differentiate between benign and malignant pigmented skin lesions.

Desmoplastic melanoma (DM) may present diagnostic challenges perhaps due to similarity of histologic mimics and even perhaps limited immunohistochemical staining. In one study, SOX10 may have shown 100% sensitivity for DM and perhaps SOX10 was negative in all histologic mimics of the dermis/subcutis, including spindle cell carcinoma, AFX and sarcomas. Although anti-S100 antibodies may typically stain DM, other melanoma markers (e.g. HMB-45 and Melan-A) are perhaps often negative.

Traditionally, melanoma markers such as S100, HMB45, MART-1 (perhaps also known as Melan-A), and Tyrosinase may have been used in a panel of antibodies to identify melanoma. Anti-S100 antibody may have been used as a screener for melanoma, and perhaps may have been a more sensitive marker compared to other melanoma markers; however, S100 may have a disadvantage of suboptimal specificity as it may stain both lymph nodes and brain, which are common sites of metastatic melanoma and its mimics. HMB45, MART-1 and Tyrosinase may perhaps be more specific than S100 protein; however, this panel of antibodies may be negative in desmoplastic melanoma and spindle cell melanoma and thus perhaps lack sensitivity.

An antibody cocktail of MART-1 and Tyrosinase, may have been shown to be a very sensitive marker of metastatic melanomas and perhaps even comparable to S100 protein (about 98% versus about 100%, respectively). However, S100 may have still been more sensitive for desmoplastic melanoma and spindle cell melanoma. The potential benefit of combining SOX10, with its sensitivity for melanoma, including desmoplastic melanoma and spindle cell melanoma, and one or more melanoma markers, perhaps even those that are not sensitive for desmoplatic melanoma or spindle cell melanoma, including perhaps MART-1 and Tyrosinase, may not be known. Such a combination may provide a superior marker for melanoma.

SOX10 may also be a neural crest transcription factor crucial for specification, maturation, and maintenance of Schwann cells and melanocytes. SOX10 may also be diffusely expressed in schwannomas and neurofibromas. Despite perhaps a well-characterized lack of specificity, pathologists may routinely employ S100 in the diagnosis of neural crest-derived tumors. Recent studies have shown that perhaps SOX10 is a reliable marker of neural crest differentiation that may be consistently expressed in schwannian and melanocytic tumors, perhaps offering advantages over S100.

SOX10 expression may be observed in myoepithelial breast cells in normal breast glands. SOX10 may have been demonstrated in basal-like, unclassified triple-negative, and in metaplastic carcinoma breast cancer types; and perhaps supports the concept that these neoplasms may show myoepithelial differentiation. In lung cancers, sustentacular cells may be found in approximately half of pulmonary carcinoid tumors. A SOX10 antibody was used to investigate perhaps 113 pulmonary cases that we not elsewhere classified (NEC). Sustentacular cells may have been observed in perhaps 66.7% of typical carcinoid (TC) and even perhaps 58.3% of atypical carcinoid (AC) cases, but may not have been observed in high-grade NECs.

SOX10 may show an increased specificity for tumors of neural crest origin, when perhaps compared with S100. In one study, SOX10 may have been positive in perhaps only 5 of 668 cases (99% specificity) in non-schwannian, non-melanocytic tumors, whereas S100 may have been positive in perhaps 53 of 668 cases (91% specificity). Therefore, SOX10 may be useful in place of, or perhaps in combination with S100, for soft tissue tumor diagnosis.

To date, most published studies may have used a goat polyclonal SOX10 for immunohistochemical (IHC) methods. Polyclonal goat antibodies may not be generally preferred for use in IHC methods, as monoclonal antibodies may be preferred, even perhaps mouse or rabbit antibodies may be preferred. Particularly for the IHC methods used in clinical diagnosis, monoclonal antibodies may be preferred, perhaps even mouse or rabbit antibodies are preferred. A clear need may exist for a marker to differentiate spindle cell and desmoplastic melanoma from other tumors and its mimics and perhaps extensive efforts to date may not have yielded such a marker. A SOX10 monoclonal antibody, would perhaps be highly valuable in the clinical setting for diagnosis.

Therefore, a clear need exists for a sensitive and even specific anti-SOX10 antibody for use in cancer diagnosis. Embodiments of the present invention provide an anti-SOX10 mouse monoclonal antibody [clone BC34] which may be highly sensitive and may even be highly specific. An example of the present invention provides a mouse monoclonal anti-SOX10 antibody that may detect the presence or absence of SOX10 protein in certain cancers, including but not limited to melanoma, spindle cell melanoma, desmoplastic melanoma, nevi, schwannomas, breast cancer, rhabdomyosarcoma, leiomyosarcoma or the like. An example of the present invention may have demonstrated excellent sensitivity for melanoma (about 105/109, about 9%) with perhaps even excellent specificity versus other normal, benign and malignant tissues. When compared to the known rabbit polyclonal (RP) anti-SOX10 antibody, the mouse monoclonal anti-SOX10 BC34 may have typically demonstrated greater sensitivity, and perhaps greater specificity, with cleaner staining patterns, perhaps with fewer artifacts, and perhaps without staining many carcinoids, while even offering the advantages of a monoclonal antibody. BC34 also may not stain some specimens, which may have been stained by the RP anti-SOX10 antibody, perhaps indicating the superior specificity of BC34 over alternatives. Therefore, a monoclonal anti-SOX10 antibody, such as BC34, may be preferred for diagnosis, compared to alternative antibodies, including alternative anti-SOX10 antibodies.

The development of an anti-SOX10 antibody may aid in the diagnosis of primary and even metastatic cancers, particularly melanoma, spindle cell melanoma, desmoplastic melanoma, nevi, schwannomas, breast cancer, rhabdomyosarcoma, leiomyosarcoma or the like. Anti-SOX10 antibodies such as mouse monoclonal anti-SOX10 antibody [BC34], with perhaps equal or superior staining sensitivity, and perhaps even superior staining specificity such as compared to alternative anti-SOX10 antibodies, including the RP anti-SOX10 antibody, have been provided in the present invention.

DISCLOSURE OF THE INVENTION

General embodiments of the present invention may include monoclonal antibodies for recognizing SOX10, methods for their preparation, use in immunohistochemistry, or the like. In embodiments, anti-SOX10 antibody clones such as the anti-SOX10 antibody clone BC34 can be obtained by immunizing Balb/C mice with one or more proteins corresponding to a subset of amino acids 147-253 of the human SOX10 protein. The SOX10 protein may be injected into the BALB/c mice, with an adjuvant, via intraperitoneal injections, perhaps about 5 times at about three week intervals. The immune reactivity to SOX10 may be assessed by direct ELISA on recombinant SOX10 protein. Mice with the highest titer may be chosen for developing hybridomas by cell fusion. A hybridoma clone demonstrating the best reactivity to SOX10 on human tissues may be chosen and may be designated as BC34. The BC34 clone may be tested for isotype and may be identified as a mouse IgG1. The BC34 antibody may be produced by large scale tissue culture of the hybridoma cells and by ascites in BALB/c mice. The supernatant and antibody ascites may be collected and the antibody may be purified by Protein A affinity column. BC34 may demonstrate specific reactivity to human SOX10 protein by ELISA, Western blotting, and even human tissues.

Anti-SOX10 antibodies such as the mouse monoclonal anti-SOX10 antibody BC34 may be useful for the detection of SOX10 in tissue samples, perhaps with several significant, but unexpected advantages over currently known antibodies to SOX10. Biological samples may be tested and may include, but are not limited to, skin tissue, lung tissue, bladder tissue, breast tissue, prostate tissue, normal tissue, neoplastic tissue, bladder tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue, breast tissue, and the like. When used in traditional immunohistochemistry procedures, anti-SOX10 antibodies such as the mouse anti-SOX10 antibody BC34 may result in nuclear staining of SOX10 with sensitivity similar or perhaps superior to that of known anti-SOX10 antibodies, which may offer significant improvements. Additionally, anti-SOX10 antibodies such as BC34 may exhibit increased specificity, perhaps as compared to other known anti-SOX10 antibodies, which may offer significant improvements. In addition to the possible advantages of being derived from a monoclonal source, anti-SOX10 antibodies such as BC34 may also offer cleaner staining, with fewer artifacts, and greater cell-type specificity, for example perhaps not staining carcinoids, when compared to other known anti-SOX10 antibodies. With anti-SOX10 antibodies such as BC34, analysis of the sample may be simplified and SOX10 expression in tumor cells may be readily identifiable, allowing diagnosis in cases that may otherwise be difficult, ambiguous, or not even possible, to diagnose.

DETAILED DESCRIPTION OF THE PREFERRED EMBODIMENTS

Figure 1:
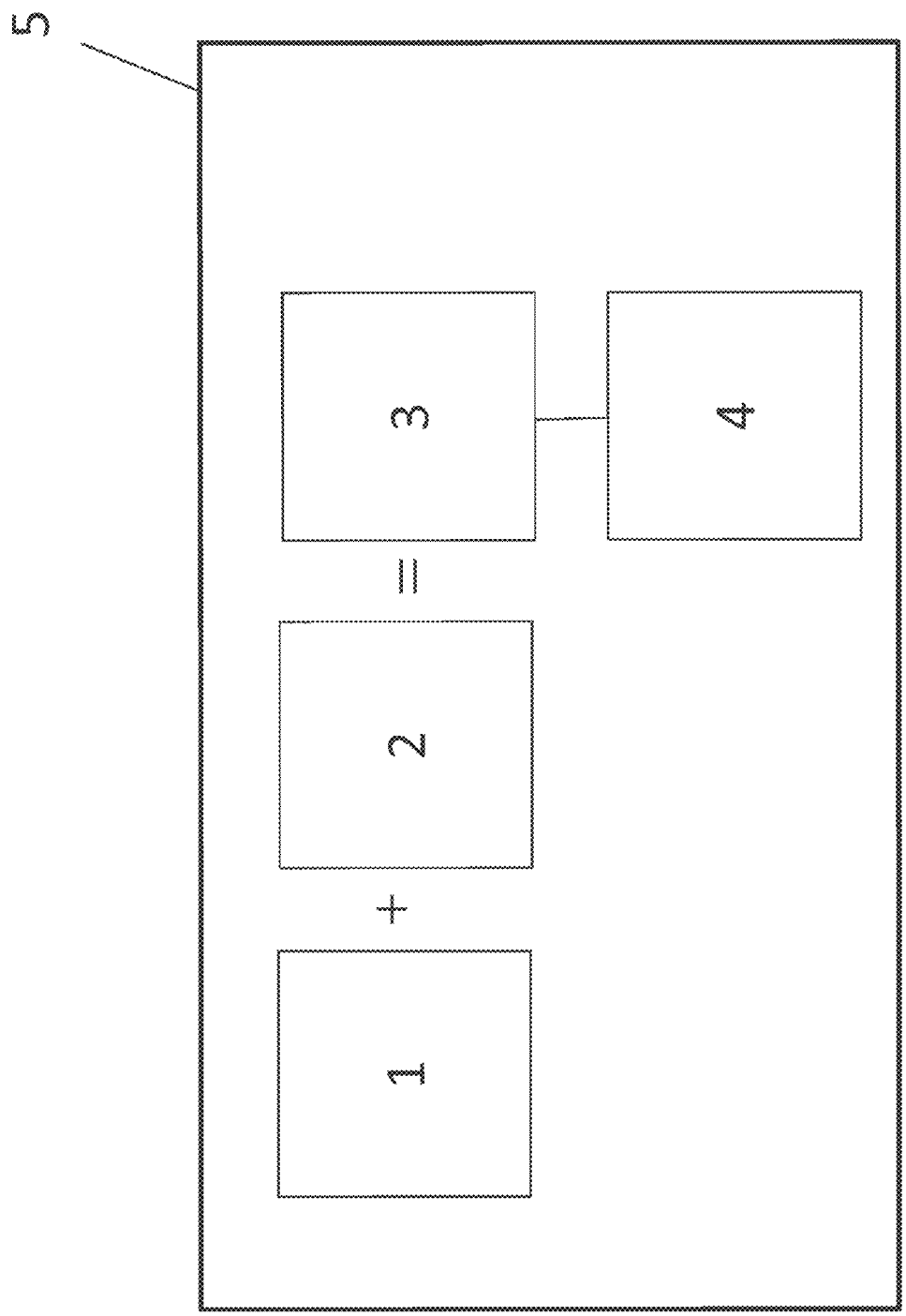
FIG. 1 shows an example of a schematic summary of a kit in accordance with various embodiments of the present invention.

As may be understood from the earlier discussion, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may provide monoclonal antibodies and methods thereof that specifically bind to SOX10 and may be used for the detection of SOX10 in the diagnosis for several types of cancers. The monoclonal antibody may be an antibody fragment, a mouse monoclonal antibody, a rabbit monoclonal antibody, a chimeric antibody, a humanized monoclonal antibody, a human monoclonal antibody, an antibody labeled with a detectable signal or stain, an antibody labeled with a toxin, or the like. The monoclonal antibody may be a chimeric antibody comprised of the variable region from one host species and the constant region from a different species, perhaps the variable region derived from a mouse monoclonal antibody known to bind SOX10 and the constant region from a rabbit IgG antibody. Systems and methods of the present invention may relate to the monoclonal antibody or its antigen binding portion capable of binding to SOX10.

Mouse monoclonal antibodies may be commonly used in immunoassay methods to identify specific analytes, including as primary antibodies in immunohistochemistry procedures. Mouse monoclonal antibodies specific for the protein target of interest can be produced using generally known procedures. Generally, exposing a mouse to the antigen of interest (e.g. a peptide fragment of the desired target or the full-length protein target) may induce an immune response in which the mouse generates multiple antibodies that bind the antigen, each of which may be produced by a particular B-cell. These B-cells may be isolated from the mouse spleen and the antibodies produced may be evaluated for their suitability as primary antibodies in IHC. After selecting the optimal antibody, the associated B-cell may be fused with a tumor cell using known procedures, perhaps resulting in a hybridoma, a new cell line that can endlessly replicate and may continuously produce the desired antibody.

Monoclonal antibodies may be preferred in certain embodiments over polyclonal antibodies for several reasons. In particular, monoclonal antibodies may be derived from a single B-cell and as such may recognize a single epitope, perhaps resulting in greater specificity. Monoclonal antibodies may also be conveniently and reproducibly generated in cell culture, perhaps resulting in a constant supply of the desired antibody. Of course, polyclonal antibodies may be utilized in other embodiments.

Anti-SOX10 antibodies such as a mouse monoclonal anti-SOX10 antibody BC34 may be produced using these general procedures and may be evaluated by immunohistochemistry for sensitivity and specificity on a variety of normal and neoplastic tissues, perhaps particularly in comparison to the previously known RP anti-SOX10 antibody.

Example of SOX10 Protein Expression:

A SOX10 recombinant protein from amino acid sequence 147 to 253 may be cloned and expressed from *E. coli*. Briefly, SOX10 cDNA may be cloned and purified. The SOX10 cDNA may be digested by restriction enzymes and ligated into the pET30a-GST vector. BL21 cells may be transformed with the construct. The colonies expressing the correct size of recombinant protein may be selected and sequenced. A further scale up production may be performed by culturing the *E. coli* in LB media containing about 0.5 mM IPTG. The final SOX10 recombinant protein may be purified and analyzed by SDS-PAGE.

Example of Host Immunization:

Female BALB/c (about 6 to about 8 weeks old) mice may be immunized intraperitoneally (i.p.) with about 100 μg human SOX10 protein per mouse in complete Freund's adjuvant. About three weeks later, the mice may be boosted with another about 100 μg human SOX10 per mouse in incomplete Freund's adjuvant about 4 more times in about 3 week intervals. Mice may be bled from the tails, and sera may be collected and stored at about −20° C. for later analysis of antibody titers by enzyme-linked immunosorbent assay (ELISA).

Example of Hybridomas:

Hybridoma producing antibodies to SOX10 may be generated by standard techniques from splenocytes of SOX10-immunized BALB/c mice. For example, splenocytes from SOX10-immunized mice may be fused to P3-X63-Ag 8.653 myeloma cells (non-secreting myeloma derived from SP2/0 Balb/c myeloma cells) by incubation with about 50% polyethylene glycol at a ratio of about 4:1. Following incubation, cells may be pelleted by centrifugation perhaps at about 300×g for about 10 minutes, washed in about 25 ml of PBS, recentrifuged, and the cell pellet may be resuspended in about 100 ml of fresh Dulbecco's Medium containing about 20% fetal bovine serum (Hyclone, Logan, Utah). Aliquots of about 100 µl can be added to each well of ten 96-well microtiter plates (Corning, Lowell, Mass.). About twenty four hours later, about 100 µl DMEM culture medium supplemented with about 1M hypoxanthine (HT), about 4 mM aminopterin and about 160 mM thymidine (HAT) can be added to each microtiter well. Media may be replaced perhaps after about 4 days with complete media (perhaps containing HAT and HT). Over the following about 10 days, media may be removed and replaced with fresh media with reduced or perhaps even no HAT and HT added. Hybridoma supernatants may be screened by ELISA for antibody reactivity to SOX10, and hybridoma clones may then be selected and stabilized perhaps by cloning twice by limiting dilution.

Hybridoma cells referred to as Anti-human SOX10 hybridoma clone BC34 have been deposited with the American Type Culture Collection (ATCC) Patent Depository in Manassas, Va. on Feb. 11, 2014 and have received ATCC Patent Deposit Designation No. PTA-120969 as shown in the attached exhibit entitled, "Budapest Restricted Certificate of Deposit" hereby incorporated by reference herein. Embodiments of the present invention may provide an antibody or fragment thereof produced by the hybridoma deposited at the ATCC and may even include a method for producing a monoclonal antibody by culturing the hybridoma cell that produces the monoclonal antibody capable of specifically recognizing SOX10 and even allowing the hybridoma to produce monoclonal antibodies.

ELISA:

Host anti-sera immune responses to SOX10 may be measured by ELISA. For example, a solution of SOX10 (about 1 µg/ml) in phosphate-buffered saline (PBS) may be used to coat about 96-well flat bottom polystyrene plates. The plates may then be blocked with about 1% bovine serum albumin (BSA)-PBS. Either diluted immune sera or hybridoma supernatants may be added and incubated at about 37° C. for about 1 hour. After washing the plates with PBS, the plates may be incubated with goat anti-mouse-HRP reagents (Jackson Labs). Incubations may be done at about 37° C. for about 30 minutes. ABTS substrate may be added to develop color and the absorbance at about 405 nm (A405) may be measured in a microtiter plate reader.

Isotype of Monoclonal Antibodies:

Anti-SOX10 antibodies such as the BC34 monoclonal antibody may be isotyped using a mouse monoclonal antibody isotyping kit (Invitrogen, Carlsbad Calif.). For example, about 100 µl of supernatant from mouse monoclonal antibody [BC34] cells may be added to the plate coated goat anti mouse IgG1, IgG2A, IgG2B, IgG3, IgM, and IgA. After about 30 minutes incubation, the plate may be washed about 3 times with PBS and may be incubated with goat anti mouse Ig-HRP reagent. ABTS substrate may be added to develop color and the absorbance at about 405 nm (A405) may be measured in a microtiter plate reader. The BC34 clone may be tested for isotype and may be identified as a mouse IgG1/kappa.

Antibody Production and Purification:

The selected hybridoma cells from clone BC34 may be cultured with DMEM culture medium supplemented with about 10% FBS or any serum-free medium. The culture supernatants may be further purified by protein A affinity column. The hybridoma cells may also be injected into pristane-primed BALB/c mice to produce antibody ascites. The antibody ascites may be further purified by protein A affinity column. IgG concentration may be measured spectrophotometrically using the extinction coefficient for mouse IgG of about 1.4 at about 280 nm. The purity of IgG may be determined by SDS-PAGE.

Western Blotting:

The purified monoclonal antibody [BC34] may be characterized by Western Blotting. Full-length SOX10 transfected cell lysates (Origene, Rockville, Md.) may be subjected to protein gel electrophoresis using about 4 to about 12% SDS-PAGE with Tris-glycine buffer and may be transferred onto nitrocellulose filters in Tris-glycine buffer. Proteins on the blots may be visualized by incubating BC34 antibody for about 60 minutes in room temperature after blocking with blocking buffer, perhaps followed by incubating with peroxidase-conjugated goat anti-mouse immunoglobulins. The blots may be detected using TMB chromogen.

Determination of VH and VL Sequences:

Total RNA may be extracted from hybridomas using Qiagen kit (USA, Gaithersburg, Md.) as per the manufacturer's instructions. Total RNA from hybridoma cells was reverse transcribed in a final volume of 20 µl containing 6 µM random primer mix (New England Biolabs Ipswich, Mass.), 0.5 mM each nucleotide dNTP Mix (Life Technologies, Grand Island, N.Y.), 5 mM DTT (Invitrogen), 40 U RNaseOUT™ Recombinant RNase Inhibitor, and 200 U Superscript III reverse transcriptase (Life Technologies, Grand Island, N.Y.). Reverse transcription (RT) reactions were performed at 42° C. for 5 min, 25° C. for 10 min, 50° C. for 60 min and 94° C. for 5 min. Mouse Igh and Igk variable regions were amplified independently by two rounds of nested PCR starting from 1 µl of cDNA as template. All PCR reactions were performed in a total volume of 20 µl containing 200 nM each primer or total primer mix (Table 1), 300 µM each dNTP (Life Technologies, Grand Island, N.Y.) and 0.1 µl of Taq DNA polymerase (Life Technologies, Grand Island, N.Y.). The first round of PCR was performed at 94°. C. for 15 min followed by 30 cycles of 94° C. for 30 s, 56° C. (Igh) or 50° C. (Igk) for 30 s, 72° C. for 55 s, and final incubation at 72° C. for 10 min. Nested second round PCR was performed with 1 µl of unpurified first round PCR product at 94° C. for 15 min followed by 30 cycles of 94° C. for 30 s, 60° C. (Igh) or 45° C. (Igk) for 30 s, 72° C. for 45 s, and final incubation at 72°. C. for 10 min. PCR products were analyzed on 2% agarose gels and cut and purified using QIAquick PCR Purification Kit (QIAGEN, Valencia, Calif.). The purified PCR products were cloned by TOPO TA Cloning System (Life Technologies, Grand Island, N.Y.). The 8 colonies were randomly selected and screened by colony PCR with M13 forward and reverse primers. PCR products were purified using QIAquick PCR Purification Kit (QIAGEN, Valencia, Calif.) and sequenced using T3 promoter sequencing primer and analysis. IMGT (the International ImMuno-GeneTics)/V-QUEST database was applied to analyze the VH and VL sequences and determine complementary determining regions (CDRs) (Table 2).

TABLE 1

```
Primer name    5'-3' sequence

Igh 1st PCR

5' MsVHE       GGGAATTCGAGGTGCAGCTGCAGGAGTCTGG    SEQ ID NO. 12
3' Cγ1 outer   GGAAGGTGTGCACACCGCTGGAC            SEQ ID NO. 13
3' Cγ2c outer  GGAAGGTGTGCACACCACTGGAC            SEQ ID NO. 14
3' Cγ2b outer  GGAAGGTGTGCACACTGCTGGAC            SEQ ID NO. 15
3' Cγ3 outer   AGACTGTGCGCACACCGCTGGAC            SEQ ID NO. 16

Igh 2nd PCR

5' MsVHE       GGGAATTCGAGGTGCAGCTGCAGGAGTCTGG    SEQ ID NO. 17
3' Cγ1 inner   GCT CAG GGA AAT AGC CCT TGA C      SEQ ID NO. 18
3' Cγ2c inner  GCT CAG GGA AAT AAC CCT TGA C      SEQ ID NO. 19
3' Cγ2b inner  ACT CAG GGA AGT AGC CCT TGA C      SEQ ID NO. 20
3' Cγ3 inner   GCT CAG GGA AGT AGC CTT TGA C      SEQ ID NO. 21

Igk 1st PCR

5' L-Vκ_3      TGC TGC TGC TCT GGG TTC CAG        SEQ ID NO. 22
5' L-Vκ_4      ATT WTC AGC TTC CTG CTA ATC        SEQ ID NO. 23
5' L-Vκ_5      TTT TGC TTT TCT GGA TTY CAG        SEQ ID NO. 24
5' L-Vκ_6      TCG TGT TKC TST GGT TGT CTG        SEQ ID NO. 25
5' L-Vκ_6,8,9  ATG GAA TCA CAG RCY CWG GT         SEQ ID NO. 26
5' L-Vκ_14     TCT TGT TGC TCT GGT TYC CAG        SEQ ID NO. 27
5' L-Vκ_19     CAG TTC CTG GGG CTC TTG TTG TTC    SEQ ID NO. 28
5' L-Vκ_20     CTC ACT AGC TCT TCT CCT C          SEQ ID NO. 29
3' mCκ         GAT GGT GGG AAG ATG GAT ACA GTT    SEQ ID NO. 30

Igk 2nd PCR

5' mVkappa     GAYATTGTGMTSACMCARWCTMCA           SEQ ID NO. 31
3' P-mJK01     CGT TTG ATT TCC AGC TTG GTG        SEQ ID NO. 32
3' P-mJK02     CGT TTT ATT TCC AGC TTG GTC        SEQ ID NO. 33
3' P-mJK03     CGT TTT ATT TCC AAC TTT GTC        SEQ ID NO. 34
3' P-mJK04     CGT TTC AGC TCC AGC TTG GTC        SEQ ID NO. 35
```

TABLE 2

| | | |
|---|---|---|
| VH, CDR1: | GFSLSTFLIG | SEQ ID NO. 6 |
| VH, CDR2: | IWWNDNK | SEQ ID NO. 7 |
| VH, CDR3: | VRMAGIGGTDAMDY | SEQ ID NO. 8 |
| VL, CDR1: | EIVEYYGTNL | SEQ ID NO. 9 |
| VL, CDR2: | AAS | SEQ ID NO. 10 |
| VL, CDR3: | QQSRKVPWT | SEQ ID NO. 11 |

BC34 variable domains were sequenced to provide isolated polynucleotides that comprise nucleic acid sequences encoding the amino acid sequences of one or more of the CDRs of the light and/or heavy chain variable regions of a monoclonal antibody described herein that binds to the SOX10 epitope QGGTAAIQAHYKSAH identified as SEQ ID NO: 3. The sequence of the variable region of the heavy chain is identified as SEQ ID NO: 1 and the sequence of the variable region of the light chain is identified as SEQ ID NO: 2. The amino acid sequence of the variable region of the heavy chain is identified as SEQ ID NO: 4 and the amino acid sequence of the variable region of the light chain is identified as SEQ ID NO: 5. An antibody or fragment thereof may include a polypeptide which may include the amino acid sequence encoded by the nucleic acid sequence of SEQ ID NO: 1 and/or SEQ ID NO: 2. An antibody or fragment thereof may include a polypeptide of the amino acid sequence of SEQ ID NO: 4 and/or SEQ ID NO: 5. An antibody or fragment thereof may include a light chain variable region having an amino acid sequence encoded by the nucleic acid sequence of SEQ ID NO: 2 and may even include a heavy chain variable region having an amino acid sequence encoded by a nucleic acid sequence of SEQ ID NO: 1. An antibody or fragment thereof may include a light chain variable region having an amino acid sequence of SEQ ID NO: 5 and may even include a heavy chain variable region having an amino acid sequence of SEQ ID NO: 4. An antibody or fragment thereof may specifically bind to at least one polypeptide of an amino acid sequence of SEQ ID NO: 3. As mentioned herein, a fragment thereof may include an antigen binding fragment thereof.

In embodiments, an antibody or fragment thereof, or even an isolated and purified nucleic acid sequence may have an amino acid sequence of at least about 70% identical to an amino acid sequence encoded by a nucleic acid sequence of SEQ ID NO: 1 and/or SEQ ID NO: 2 and/or the amino acid sequence of SEQ ID NO: 3. In embodiments, an antibody or fragment thereof may have an amino acid sequence of at least about 70% identical to an amino acid sequence of SEQ ID NO: 4 and/or SEQ ID NO: 5 and/or the amino acid sequence of SEQ ID NO: 3. An antibody or fragment thereof may specifically bind to at least one polypeptide with an amino acid sequence that is at least about 70% identical to residues of SEQ ID NO: 3. Other percentages may include, but are not limited to, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and perhaps even at least about 99%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or the like.

In other embodiments, an antibody or fragment thereof may include a polypeptide of the amino acid sequence of SEQ ID NO: 6, 7, 8, 9, 10, and/or 11 and any combination thereof. An antibody or fragment thereof may include a light chain variable region having an amino acid sequence of SEQ ID NO: 9, 10, and/or 11 or any combination thereof and may even include a heavy chain variable region having an amino acid sequence of SEQ ID NO: 6, 7, and/or 8 or any combination thereof.

In reference to Table 2 and SEQ ID NOS. 6-11, an antibody or fragment thereof may have an amino acid sequence of perhaps at least about 2% up to at least about 26% identical to an amino acid sequence of SEQ ID NO: 4 and/or SEQ ID NO: 5. Other percentages may include, but are not limited to, at least about 2%, at least about 2.7%, at least about 3%, at least about 4%, at least about 5%, at least about 5.7%, at least about 6%, at least about 7%, at least about 8%, at least about 8.1%, at least about 9%, at least about 10%, at least about 10.8%, at least about 11%, at least about 11.4%, at least about 11.7%, at least about 12%, at least about 13%, at least about 13.9%, at least about 14%, at least about 15%, at least about 16%, at least about 17%, at least about 17.1%, at least about 17.2%, at least about 18%, at least about 19%, at least about 19.6%, at least about 19.8%, at least about 20%, at least about 21%, at least about 22%, at least about 23%, at least about 24%, at least about 25%, at least about 25.4%, at least about 26%, at least about 30%; between about 2% and about 70%, about 2%, about 2.7%, about 3%, about 4%, about 5%, about 5.7%, about 6%, about 7%, about 8%, about 8.1%, about 9%, about 10%, about 10.8%, about 11%, about 11.4%, about 11.7%, about 12%, about 13%, about 13.9%, about 14%, about 15%, about 16%, about 17%, about 17.1%, about 17.2%, about 18%, about 19%, about 19.6%, about 19.8%, about 20%, about 21%, about 22%, about 23%, about 24%, about 25%, about 25.4%, about 26%, about 30%, or the like.

Epitope Mapping of the Mouse Anti-SOX10 [BC34] Binding Sequence:

In order to determine the peptide sequence of SOX10 that is recognized by anti-SOX10 antibodies such as BC34, epitope mapping may be conducted perhaps using two assays: direct ELISA and even dot blot. In an ELISA assay, the sensitivity and specificity of the anti-SOX10 [BC34] antibody may be determined by measuring the antibody titer at about 1:500 and about 1:1000. Overlapping peptides at a length of about 15 amino acids each, covering the human SOX10 protein sequence from perhaps 147 to 253 amino acids, may be used to determine a sequence of BC34 binding.

The epitope for BC34 was shown to be included in the residues 196-211 amino acids of SOX10, which is QGG-TAAIQAHYKSAH identified as SEQ ID NO: 3. The epitope of the mouse monoclonal SOX10 antibody, or a portion thereof, may be a useful antigen for the production of new monoclonal antibodies, including production in species other than mouse (e.g. rabbit, goat, horse, chicken, etc.). Of course, a polyclonal antibody may specifically bind to an epitope in SEQ ID NO: 3, which relates to residues 196-211 of the SOX10 protein.

For direct ELISA protocol, the plates may be first coated with about 100 µl of SOX10 peptides at about 5 m/mL in coating buffer (pH about 9.5) overnight at about 4° C., followed by blocking (about 3% BSA) at about 200 µl/well for about 1 hour at room temperature. The plates may be incubated with purified SOX10 antibody at about 100 ng/mL and about 200 ng/mL separately for about 1 hour at about room temperature on an ELISA-plate shaker. Then the plates may be washed perhaps five times with PBST (about 300 µl/well) followed by the addition of goat anti-mouse IgG-HRP to the plates and incubation for about 1 hour on a plate-shaker. The plates may then be washed with PBST (about 300 µl/well) and blotted to dry, and TMB may be added at about 100 µl/well, developed for about 5 min on a shaker, and may even be followed by a stop solution (about 50 µl/well). Absorbance may be measured at about 450 nm on an ELISA plate reader perhaps according to the manufacturer's recommendation.

For the dot blot assay, a nitrocellulose membrane may be blotted with about 1 µl at a concentration of about 1 mg/ml the peptide, quadruplicates per peptide. This membrane may be incubated for about 1 hour at room temperature until it may be completely dry. The membrane may be blocked with about 3% BSA in TBST (e.g., about 50 mM Tris, about 0.5 M NaCl, about 0.05% Tween-20, pH about 7.4) for about 1 hour at room temperature, then mouse anti SOX10 antibody [BC34] may be added at about 200 ng/ml for about 1 hr at RT in TBST. Then the membrane may be washed for about 3 times (about 10 minutes each) in TBST on an orbital shaker, followed by incubating with secondary antibody goat anti mouse IgG1-AP for about 1 hour at room temperature in TBST. The membrane may be washed perhaps about 3 times (about 10 minutes each) in TBST on a rocker. The binding may be detected by adding Western Glo Chemiluminescent detection reagents and exposing to film.

IHC Method with Anti-SOX10 BC34:

Immunohistochemistry using anti-SOX10 antibodies such as the mouse monoclonal anti-SOX10 antibody BC34 may be performed on formalin-fixed paraffin embedded (FFPE) tissue samples using procedures generally known to those in the art, as generally exemplified by the following non-limiting examples (e.g., washes with Tris-buffered saline, pH about 7.6, between steps):

1) Sections (~5 m) of formalin fixed paraffin-embedded tissues may be mounted on commercially available microscope slides perhaps coated with polylysine.
2) Sections may be deparaffinized (using xylenes or a xylene-substitute) and may be rehydrated perhaps through a series of alcohol/water solutions, perhaps followed by blocking of endogenous peroxidases perhaps with about 3% hydrogen peroxide solution.
3) Samples may be subjected to heat-induced antigen retrieval using a citrate buffer in a pressure cooker (Diva, Decloaking Chamber; Biocare Medical) and may be heated to about 125° C. for about 30 seconds. [Other antigen retrieval methods known to those skilled in the art (e.g., steamer, microwave oven, enzyme, or the like) may also be acceptable.] Tissues may be allowed to cool for about 10 minutes and then may be rinsed with deionized water.
4) A protein blocking solution (Background Punisher, Biocare Medical) may be applied to the tissue for about 10 minutes.
5) The SOX10 antibody BC34 may be applied in a tris-buffered solution (pH about 6.2) with bovine serum albumin as carrier protein for about 30 minutes. The SOX10 antibody BC34 may be diluted perhaps 1:10,000.
6) Detection of the SOX10 antibody perhaps with a horseradish peroxidase (HRP) conjugated secondary antibody (MACH 2 Mouse HRP-Polymer Detection, Biocare Medical) may be accomplished by application of goat anti-mouse-HRP conjugate for about 30 minutes. In another example, detection of the SOX10 antibody perhaps with a horseradish peroxidase (HRP) conjugated secondary antibody (MACH 4 Universal HRP-Polymer Detection, Biocare Medical) may be accomplished in two steps. An initial application of a rabbit anti-mouse IgG antibody for about 10 minutes may be followed by incubation with a goat anti-rabbit-HRP conjugate for about 10 minutes.
7) In perhaps a final detection step, 3,3'-diaminobenzidine (DAB) in buffer perhaps containing about 0.02% hydrogen peroxide (Betazoid DAB, Biocare Medical) may be applied. The oxidation of DAB through an HRP-mediated mechanism may result in precipitation of a brown, chromogenic product, perhaps allowing identification of sites of SOX10 expression.
8) Slides may be briefly counterstained perhaps in a modified Mayer's hematoxylin.

IHC Method with Anti-SOX10 BC34 Using Alkaline Phosphatase Detection and Fast Red Chromogen:

IHC using BC34 may also be performed as described above, using an alkaline phosphatase (AP) conjugated secondary antibody and a Fast Red chromogen. For example, detection of the SOX10 antibody perhaps with an AP conjugated secondary antibody (MACH 2 Mouse AP-Polymer Detection, Biocare Medical) may be accomplished by application of goat anti-mouse-AP conjugate for about 30 minutes. In perhaps a final detection step, a naphthol phosphate salt (e.g. naphthol phosphate AS-TR) and a diazonium salt (e.g. Fast Red KL) in buffer (Vulcan Fast Red, Biocare Medical) may be applied. The cleavage of the phosphate by alkaline phosphatase, followed by reaction of the resulting naphthol with the diazonium salt may result in precipitation of a red, chromogenic product, perhaps allowing identification of sites of SOX10 expression.

IHC Method with SOX10 Antibody BC34, Tyrosinase Antibody T311, and MART-1 Antibodies M2-7C10 and M2-9E3:

IHC may be performed as described above using a primary antibody cocktail perhaps comprised of SOX 10 [BC34], Tyrosinase antibody [T311], and perhaps even MART-1 antibodies [M2-7C10] and [M2-9E3]. Detection of each antibody may be accomplished with a horseradish peroxidase (HRP) conjugated secondary antibody (MACH 4 Universal HRP-Polymer Detection, Biocare Medical) perhaps in two steps. An initial application of a rabbit anti-mouse IgG antibody for about 10 minutes may be followed by incubation with a goat anti-rabbit-HRP conjugate for about 10 minutes, followed by visualization with DAB.

Results of IHC Staining with Mouse Monoclonal Anti-SOX10 Antibody BC34:

Using the above protocol, a variety of normal and neoplastic tissues were evaluated for SOX10 expression using BC34 and in some cases compared to staining patterns using a RP anti-SOX10 antibody. All antibodies were optimized for titer (e.g., concentration) using methods well known to those in the art. For example, various antibody titers were evaluated to maximize staining intensity, perhaps while minimizing or even eliminating background staining. For each antibody, the titer that provided the maximum staining intensity, perhaps with the minimal background staining, was used.

Figure 3:
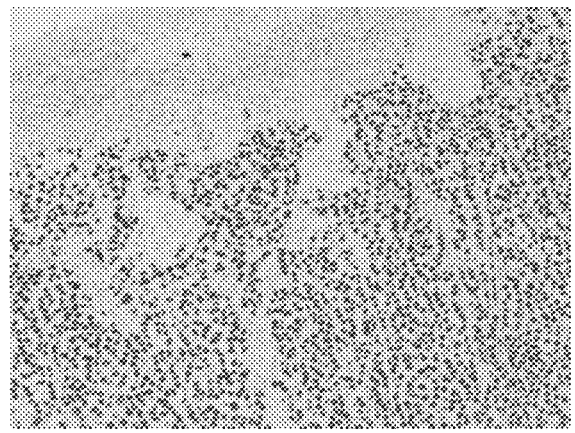
FIG. 3 shows a black and white version of an example of anti-SOX10 antibody BC34 staining a case of melanoma of the chest wall (10.times. magnification).
Figure 4:
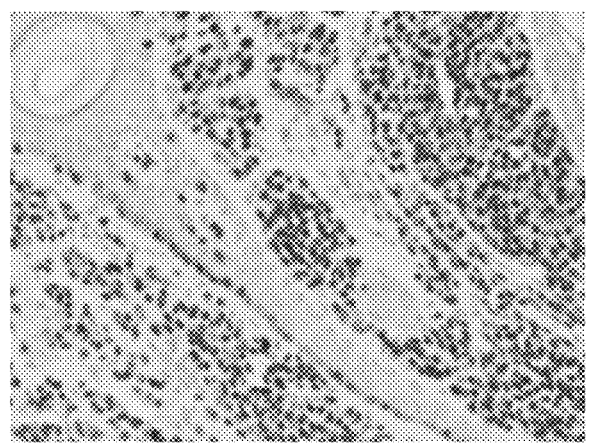
FIG. 4 shows a black and white version of an example of anti-SOX10 antibody BC34 staining a case of melanoma of the scalp (20.times. magnification).
Figure 5:
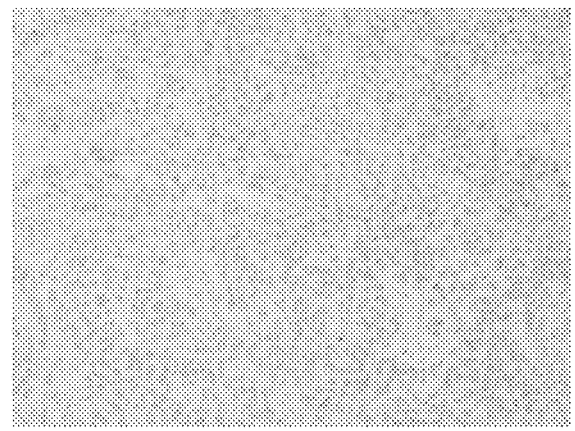
FIG. 5 shows a black and white version of an example of anti-SOX10 antibody BC34 staining a case of melanoma of the shoulder (10.times. magnification). Reduced staining, or perhaps and absence of staining may be observed in this sample.
Figure 6:
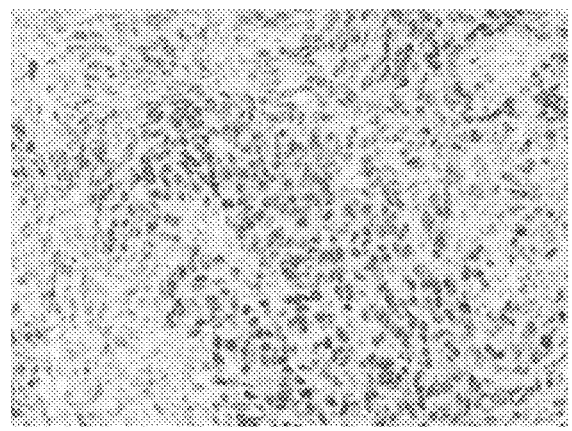
FIG. 6 shows a black and white version of an example of anti-SOX10 antibody BC34 staining a case of metastatic melanoma in a lymph node (20.times. magnification).
Figure 7:
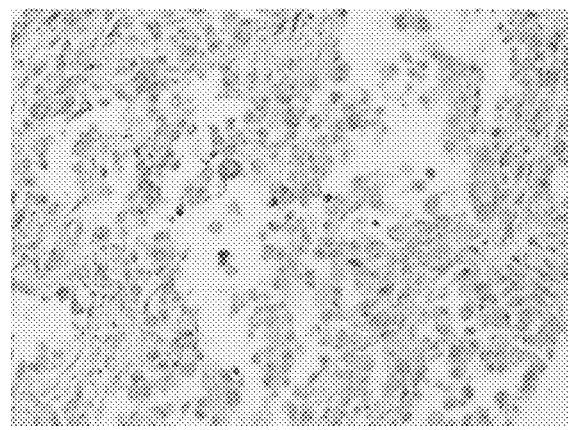
FIG. 7 shows a black and white version of an example of anti-SOX10 antibody BC34 staining a case of balloon cell melanoma (10.times. magnification).
Figure 8:
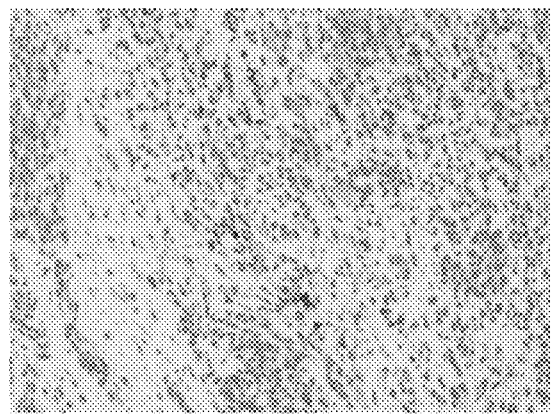
FIG. 8 shows a black and white version of an example of anti-SOX10 antibody BC34 staining a case of epithelioid melananoma (10.times. magnification).
Figure 10:
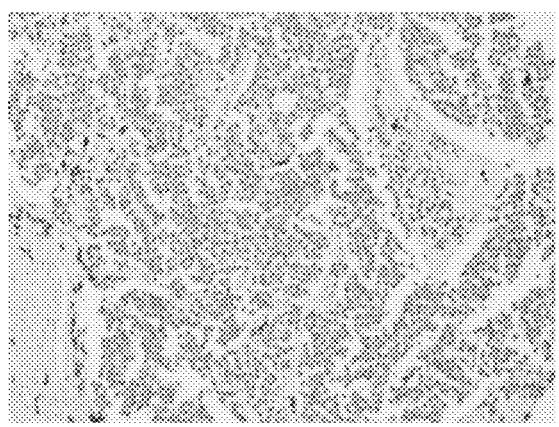
FIG. 10 shows a black and white version of an example of anti-SOX10 antibody BC34 staining a case of perivascular melanoma (10.times. magnification).
Figure 11:
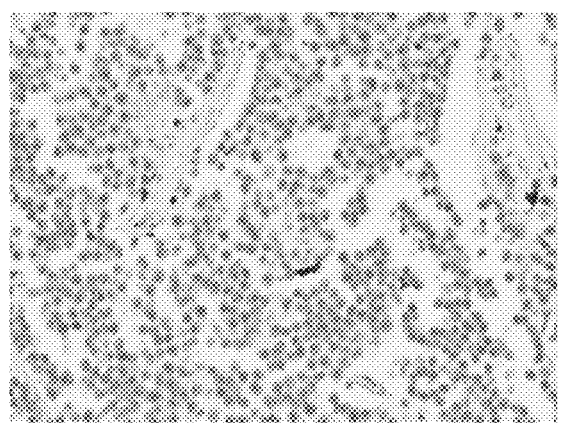
FIG. 11 shows a black and white version of an example of anti-SOX10 antibody BC34 staining a case of perivascular melanoma (20.times. magnification).
Figure 12:
FIG. 12 shows a black and white version of an example of anti-SOX10 antibody BC34 staining a case of rhabdoid melanoma (10.times. magnification).
Figure 13:
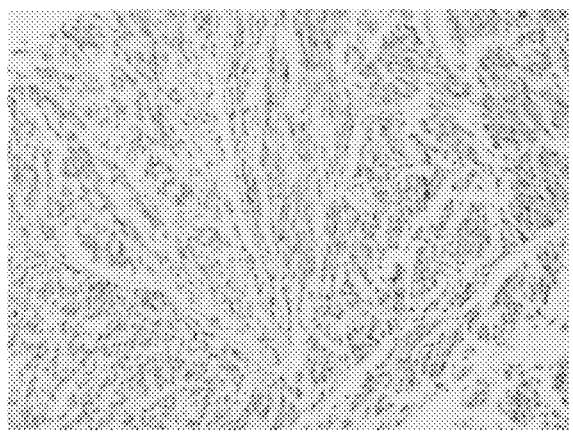
FIG. 13 shows a black and white version of an example of anti-SOX10 antibody BC34 staining a case of sarcomatoid melanoma (10.times. magnification).
Figure 14:
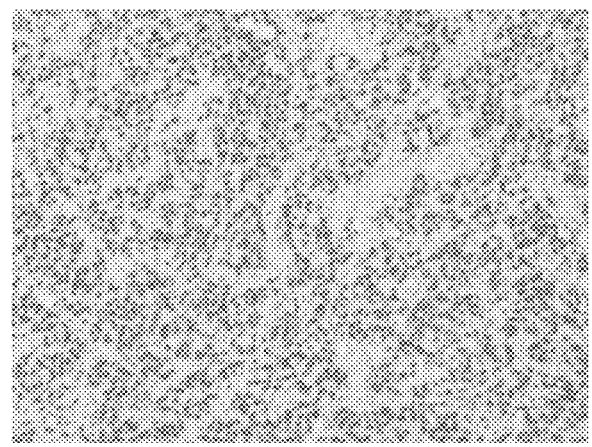
FIG. 14 shows a black and white version of an example of anti-SOX10 antibody BC34 staining a case of plasmacytoid melanoma (10.times. magnification).

Staining with BC34 may be observed in various cases of melanoma, as shown in FIGS. 3-5. In fact, melanoma metastatic to the lymph node may also be identified by BC34 (FIG. 6). In some cases, particularly cases of melanoma, where endogenous pigments of melanocytes may be present, staining with a red chromogen may be advantageous. BC34 may stain cases of balloon cell melanoma (FIG. 7), epithelioid melanoma (FIG. 8), perivascular melanoma (FIGS. 10-11), rhabdoid melanoma (FIG. 12), sarcomatoid melanoma (FIG. 13), and plasmacytoid melanoma (FIG. 14).

Figure 9:
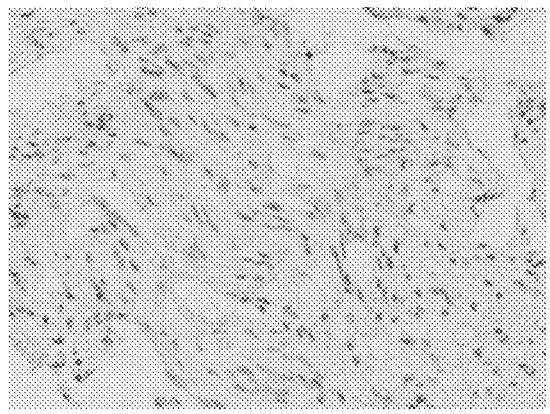
FIG. 9 shows a black and white version of an example of anti-SOX10 antibody BC34 staining a case of peripheral nerve tumor (20.times. magnification).
Figure 15:
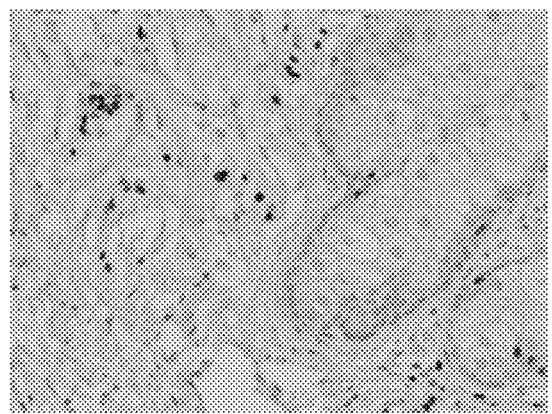
FIG. 15 shows a black and white version of an example of anti-SOX10 antibody BC34 staining a case of compound nevus of skin (20.times. magnification).
Figure 16:
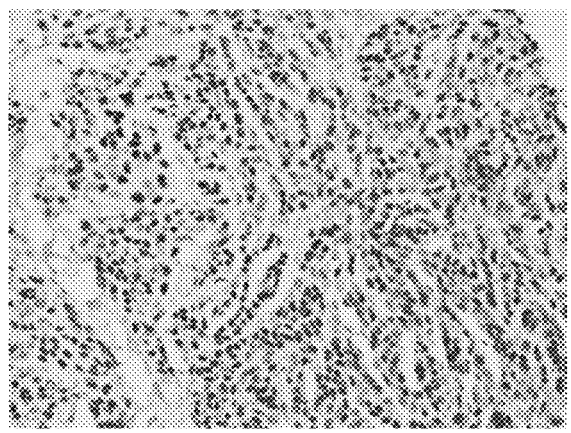
FIG. 16 shows a black and white version of an example of anti-SOX10 antibody BC34 staining a case of intradermal nevus of the cheek (20.times. magnification).
Figure 17:
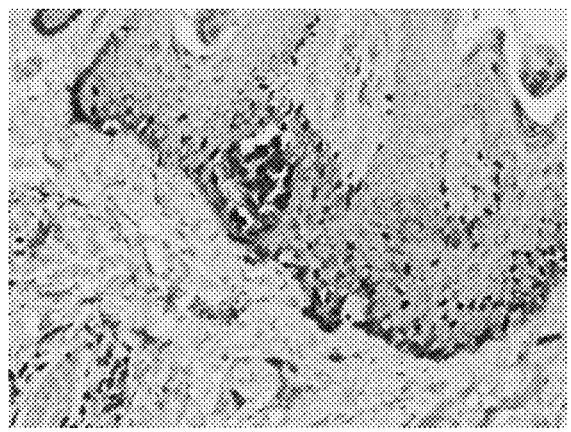
FIG. 17 shows a black and white version of an example of anti-SOX10 antibody BC34 staining a case of junctional nevus of skin (20.times. magnification).
Figure 18:
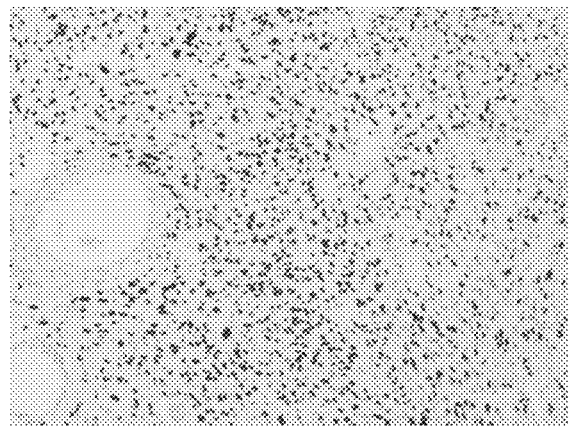
FIG. 18 shows a black and white version of an example of anti-SOX10 antibody BC34 staining a case of schwannoma (10.times. magnification).
Figure 19:
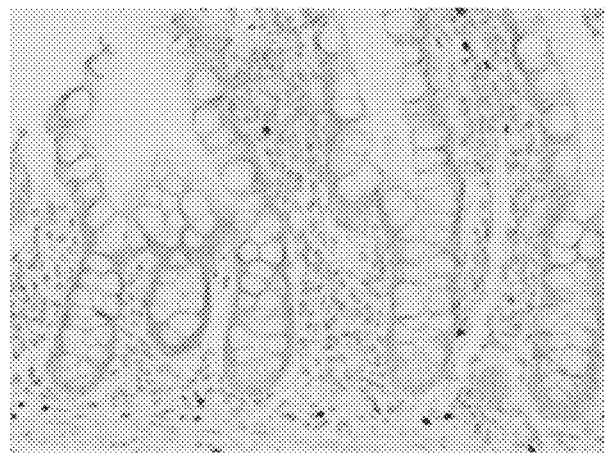
FIG. 19 shows a black and white version of an example of anti-SOX10 antibody BC34 staining argentaffin cells in normal colon (20.times. magnification).
Figure 20:
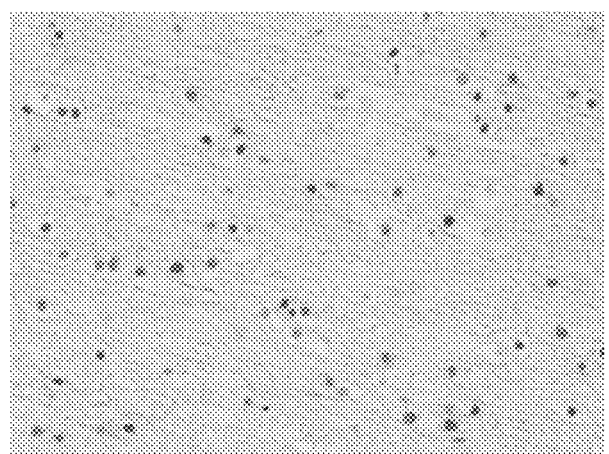
FIG. 20 shows a black and white version of an example of anti-SOX10 antibody BC34 staining normal brain neurons (20.times. magnification).
Figure 21:
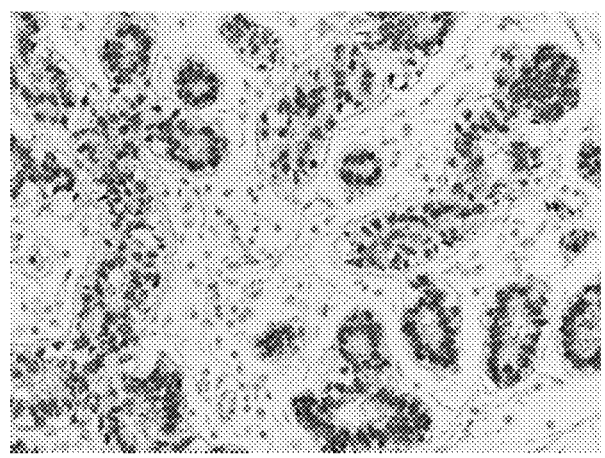
FIG. 21 shows a black and white version of an example of anti-SOX10 antibody BC34 staining a myoepithelial cells in normal breast glands (20.times. magnification).
Figure 22:
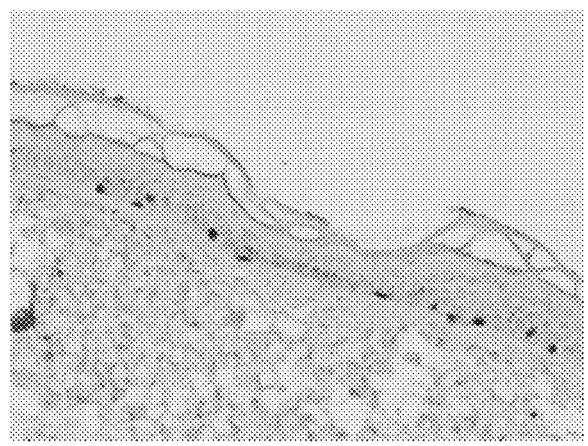
FIG. 22 shows a black and white version of an example of anti-SOX10 antibody BC34 staining normal skin (20.times. magnification).
Figure 23:
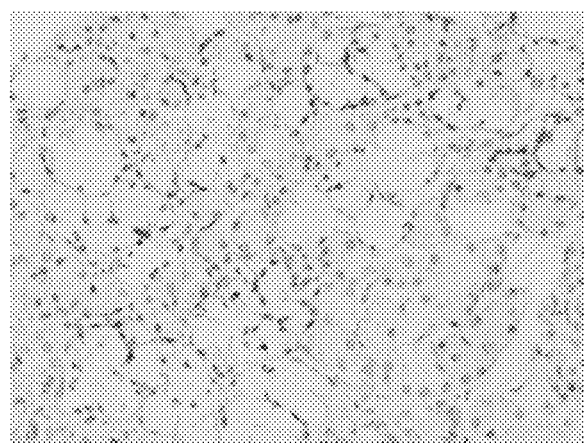
FIG. 23 shows a black and white version of an example of anti-SOX10 antibody BC34 staining normal salivary gland (20.times. magnification).

Staining with BC34 may also be observed in peripheral nerve tumors (FIG. 9), as well as cases of nevus (FIGS. 15-17). Schwannomas may also stain with BC34 (FIG. 18).

In normal tissues, Argentaffin cells in normal colon, normal brain neurons, myoepithelial cells of breast glands, normal skin, and normal salivary glands may stain with BC34 (FIGS. 19-23).

Figure 24:
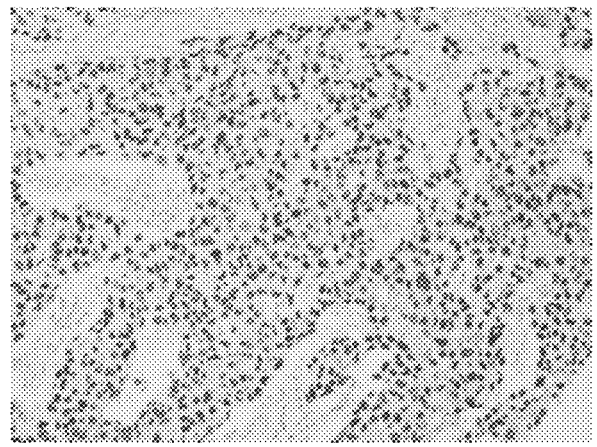
FIG. 24 shows a black and white version of an example of anti-SOX10 antibody BC34 staining breast tissue, perhaps breast cancer.
Figure 25:
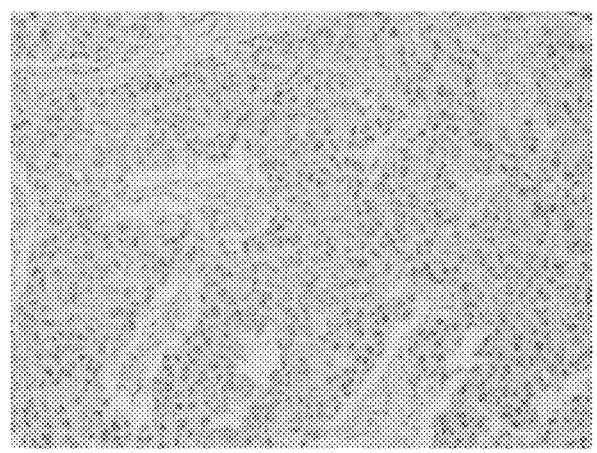
FIG. 25 shows a black and white version of an example of RP anti-SOX10 antibody staining the same breast specimen of FIG. 24. Staining may be less intense that that observed with BC34 in FIG. 24.

Staining with BC34 may be superior to that of the RP anti-SOX10 antibody, particularly in cases where BC34 exhibits greater sensitivity, or perhaps increased staining intensity, as well as cases where BC34 is perhaps more specific. For example, BC34 may exhibit more intense staining in cases of breast cancer (FIG. 24), compared to the RP anti-SOX10 antibody (FIG. 25).

Figure 26:
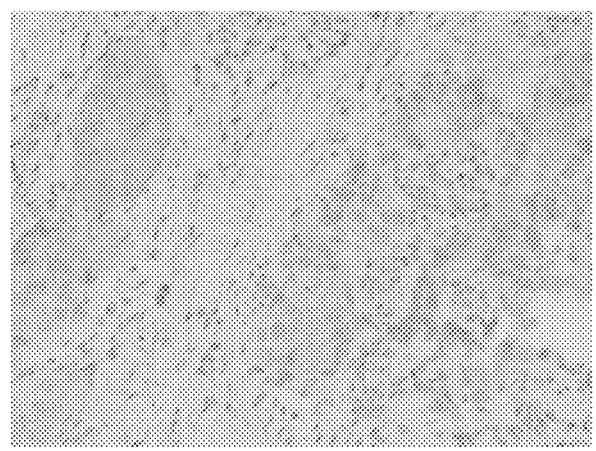
FIG. 26 shows a black and white version of an example of anti-SOX10 antibody BC34 staining lung tissue, perhaps lung adenocarcinoma. Staining may be reduced, or perhaps absent, particularly when compared to FIG. 27.
Figure 27:
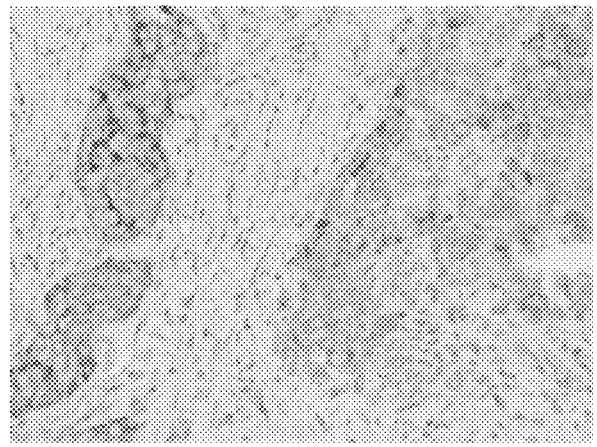
FIG. 27 shows a black and white version of an example of RP anti-SOX10 antibody staining the same lung specimen of FIG. 26. Cytoplasmic staining may be observed in this sample, in contrast to the nuclear staining expected for SOX10.

In lung adenocarcinoma, BC34 may demonstrate improved specificity compared to the RP anti-SOX10 antibody. For example, staining with BC34 may be reduced, or perhaps absent (FIG. 26), in cases where the RP anti-SOX10 antibody produces cystoplasmic staining, which would not be consistent with SOX10 expression (FIG. 27).

Figure 28:
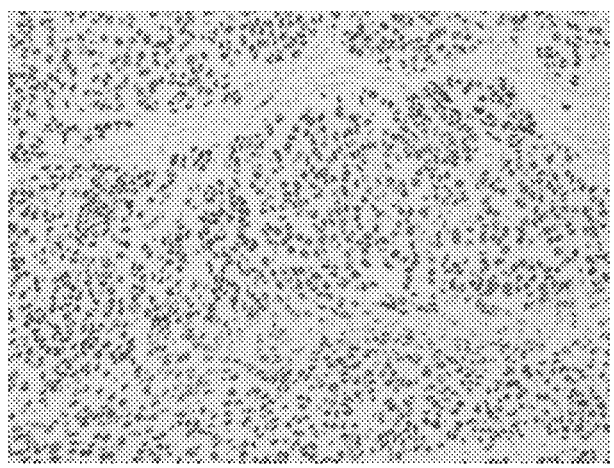
FIG. 28 shows a black and white version of an example of anti-SOX10 antibody BC34 staining melanoma. Staining may perhaps be more intense than that observed in FIG. 29.
Figure 29:
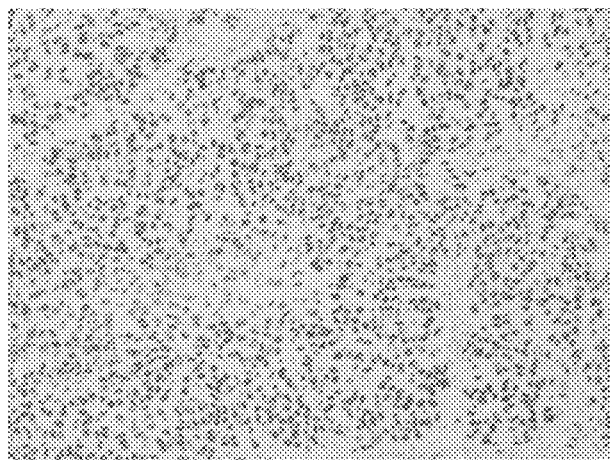
FIG. 29 shows a black and white version of an example of RP anti-SOX10 antibody staining the same melanoma specimen of FIG. 28. Staining may be less intense that that observed with BC34 in FIG. 28.
Figure 30:
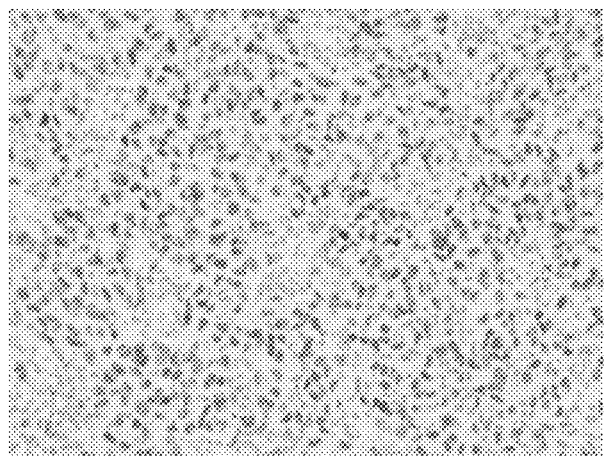
FIG. 30 shows a black and white version of an example of anti-SOX10 antibody BC34 staining melanoma. Staining may perhaps be more intense than that observed in FIG. 31.
Figure 31:
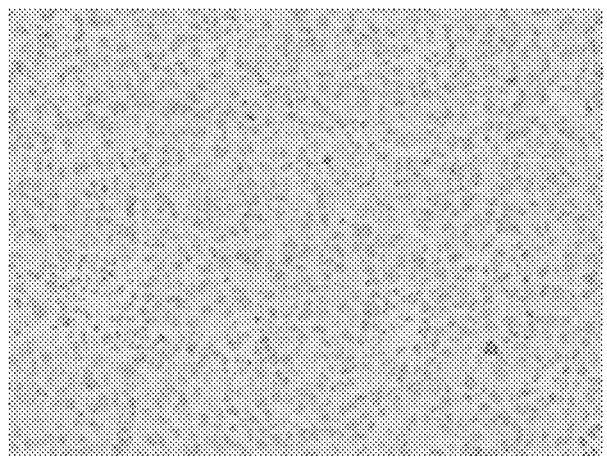
FIG. 31 shows a black and white version of an example of RP anti-SOX10 antibody staining the same breast specimen of FIG. 30. Staining may be reduced, or perhaps absent, compared that that observed with BC34 in FIG. 30.
Figure 32:
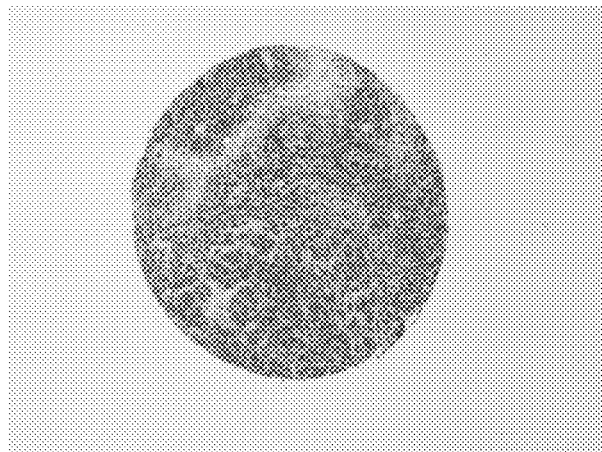
FIG. 32 shows a black and white version of an example of anti-SOX10 antibody BC34 staining melanoma. Staining may perhaps be more intense than that observed in FIG. 33.
Figure 33:
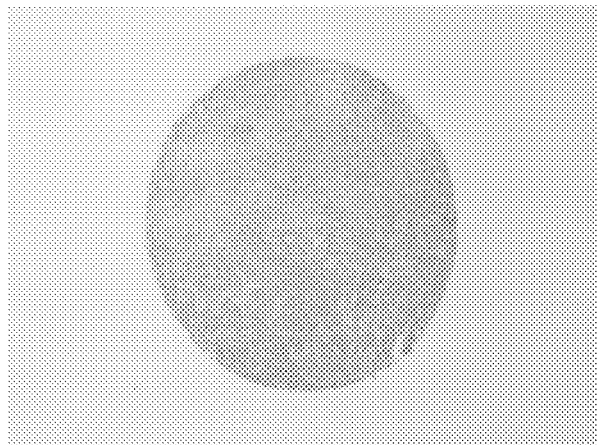
FIG. 33 shows a black and white version of an example of RP anti-SOX10 antibody staining the same breast specimen of FIG. 32. Staining may be reduced, or perhaps absent, compared that that observed with BC34 in FIG. 32.

Cases of melanoma may also demonstrate more intense staining with BC34 (FIGS. 28, 30, and 32), compared to that of the RP anti-SOX10 antibody on the same specimens, where staining may be reduced, or perhaps even absent, when using the RP anti-SOX10 antibody (FIGS. 29, 31, and 33).

Figure 34:
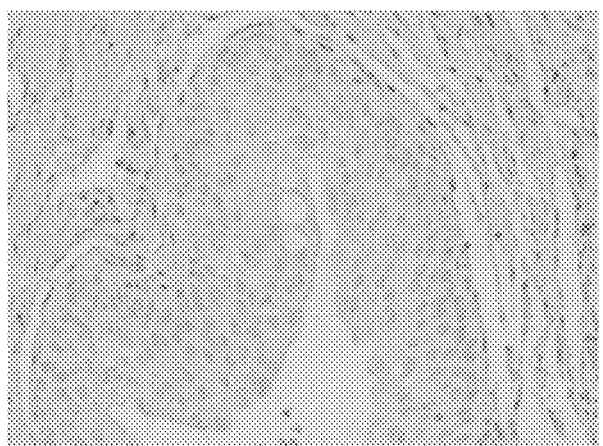
FIG. 34 shows a black and white version of an example of anti-SOX10 antibody BC34 staining normal bladder. Staining may be reduced, or perhaps absent, particularly when compared to FIG. 35.
Figure 35:
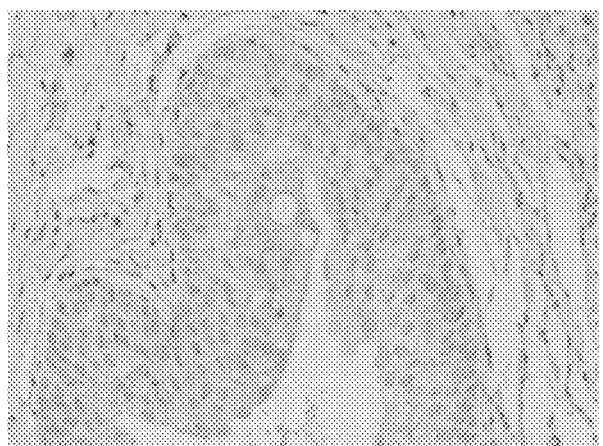
FIG. 35 shows a black and white version of an example of RP anti-SOX10 antibody staining the same bladder specimen of FIG. 34. Cytoplasmic staining may be observed in this sample, in contrast to the nuclear staining expected for SOX10.

In normal bladder, BC34 may demonstrate improved specificity compared to the RP anti-SOX10 antibody. For example, staining with BC34 may be reduced, or perhaps absent (FIG. 34), in cases where the RP anti-SOX10 antibody produces cystoplasmic staining, which would not be consistent with SOX10 expression (FIG. 35).

Figure 36:
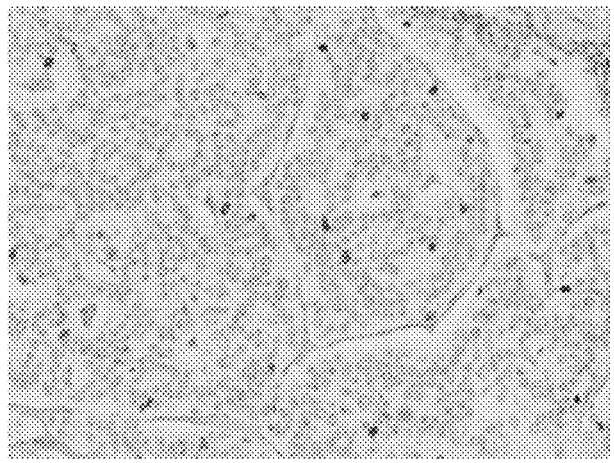
FIG. 36 shows a black and white version of an example of anti-SOX10 antibody BC34 staining intestinal carcinoids (20.times. magnification).
Figure 37:
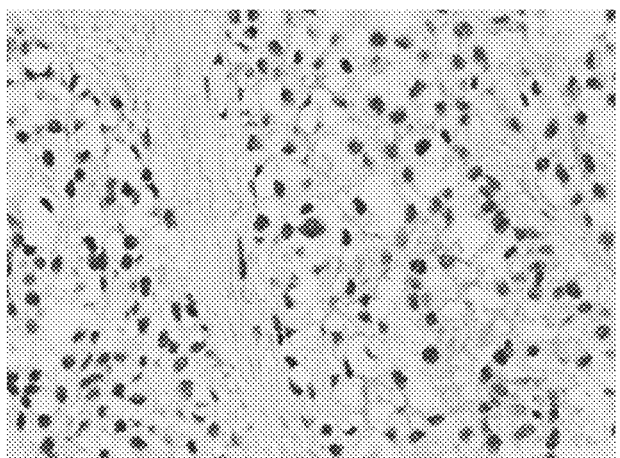
FIG. 37 shows a black and white version of an example of anti-SOX10 antibody BC34 staining a case of alveolus rhabdomyosarcoma (20.times. magnification).
Figure 38:
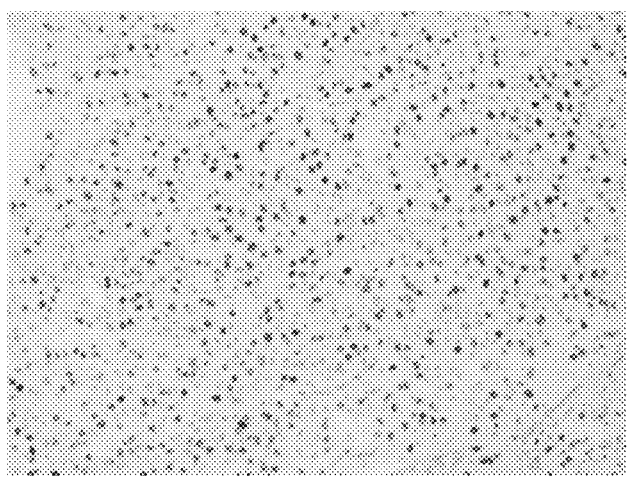
FIG. 38 shows a black and white version of an example of anti-SOX10 antibody BC34 staining a case of astrocytoma (10.times. magnification).
Figure 39:
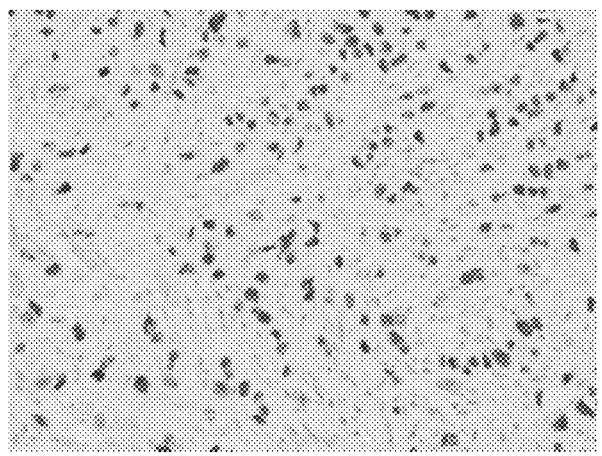
FIG. 39 shows a black and white version of an example of anti-SOX10 antibody BC34 staining a case of breast cancer (20.times. magnification).
Figure 40:
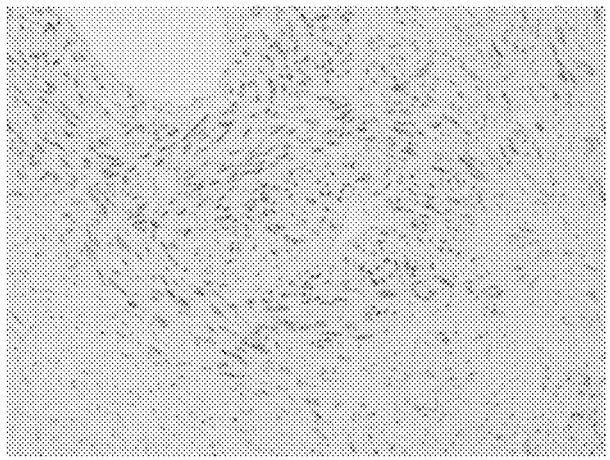
FIG. 40 shows a black and white version of an example of anti-SOX10 antibody BC34 staining a case of intermediate grade II leiomyosarcoma (10.times. magnification).
Figure 41:
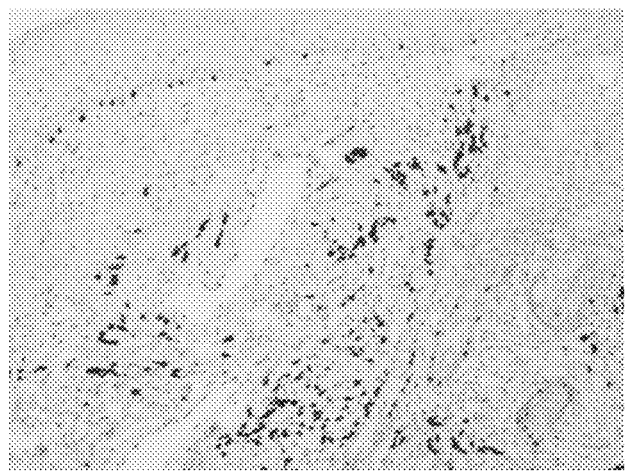
FIG. 41 shows a black and white version of an example of anti-SOX10 antibody BC34 staining a case of desmoplastic melanoma (10.times. magnification).
Figure 42:
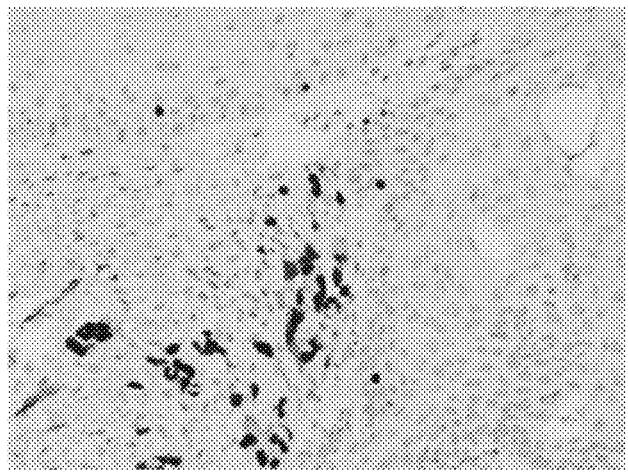
FIG. 42 shows a black and white version of an example of anti-SOX10 antibody BC34 staining a case of desmoplastic melanoma (20.times. magnification).
Figure 43:
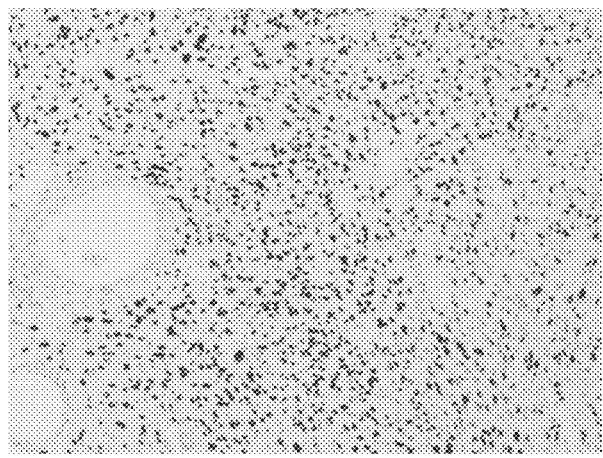
FIG. 43 shows a black and white version of an example of anti-SOX10 antibody BC34 staining a case of benign schwannoma (10.times. magnification).

BC34 may also stain other neoplastic tissues, including perhaps intestinal carcinoids (FIG. 36), alveolus rhabdomyosarcoma (FIG. 37), astrocytoma (FIG. 38), breast cancer (FIG. 39), leiomyosarcoma (FIG. 40). BC34 may also stain benign schwannoma (FIG. 43).

Figure 44:
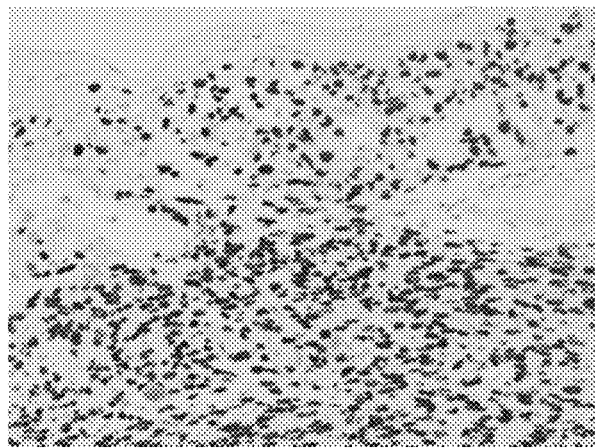
FIG. 44 shows a black and white version of an example of anti-SOX10 antibody BC34 staining a case of spindle cell melanoma (20.times. magnification).
Figure 45:
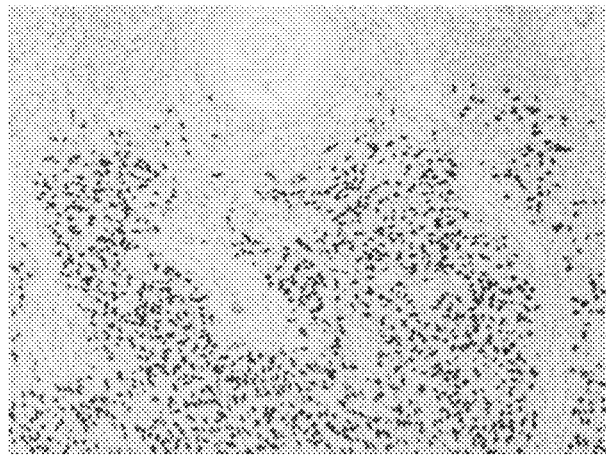
FIG. 45 shows a black and white version of an example of anti-SOX10 antibody BC34 staining a case of spindle cell melanoma (10.times. magnification).
Figure 46:
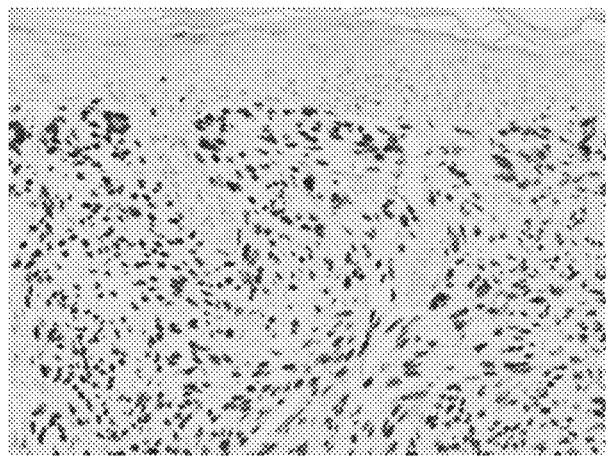
FIG. 46 shows a black and white version of an example of anti-SOX10 antibody BC34 staining a case of spindle cell melanoma (20.times. magnification).

Staining with BC34 may also be observed in desmoplastic melanomas (FIGS. 35-36) and spindle cell melanomas (FIGS. 44, 46).

Figure 47:
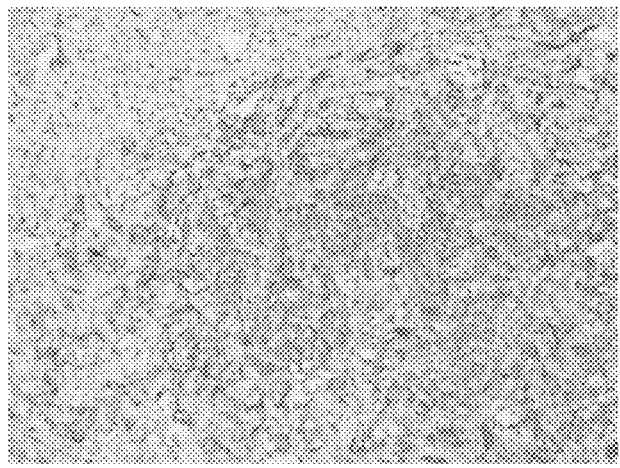
FIG. 47 shows a black and white version of an example of an antibody cocktail of Tyrosinase+MART-1 staining a case of melanoma.
Figure 48:
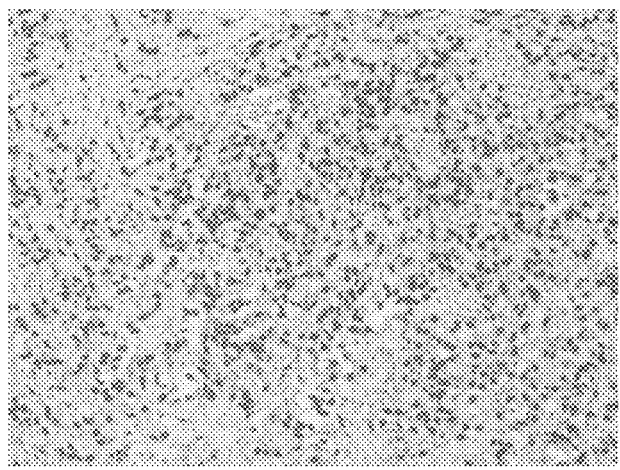
FIG. 48 shows a black and white version of an example of SOX10 [BC34] staining the same case of melanoma shown in FIG. 47.

Melanoma may also be stained by Tyrosinase and MART-1, including a cocktail of Tyrosinase+MART-1 (FIG. 47). BC34 may also stain the same cases of melanoma (FIG. 48). A cocktail of SOX10 [BC34]+Tyrosinase+MART-1 may stain melanoma (FIGS. 49, 50) and perhaps be more sensitive than S100 alone, or Tyrosinase+MART-1 alone (Table 4). In cases such as that shown in FIG. 50, SOX10 and Tyrosinase+MART-1 may stain different areas of the tumor, which may be identified by the nuclear staining of SOX10 and the cytoplasmic staining of Tyrosinase+MART-1. Differential staining in a tumor may perhaps indicate the presence of more than one clone in the tumor.

Figure 51:
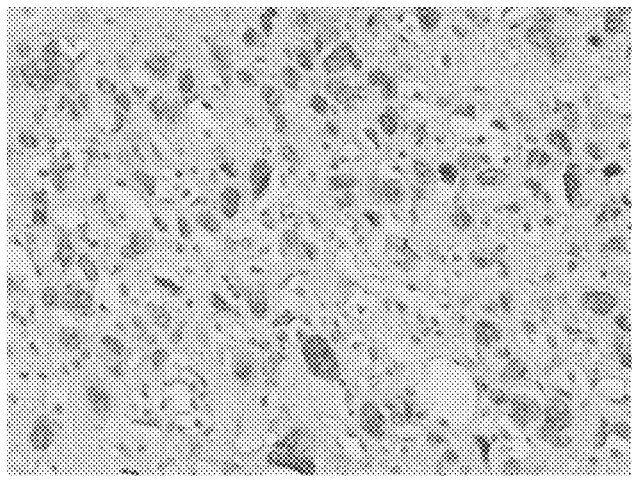
FIG. 51 shows a color version of an example of BC34 staining a case of melanoma.
Figure 52:
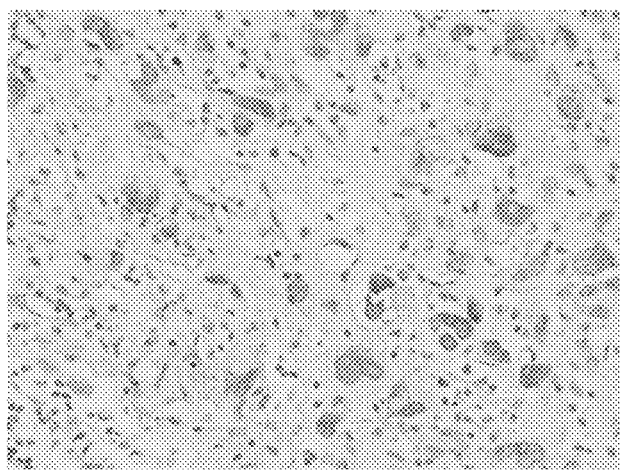
FIG. 52 shows a black and white version of the same case of melanoma shown in FIG. 51 stained with a cocktail of Tyrosinase+MART-1. Perhaps reduced staining or no staining may be present, although pigmented melanocytes may be observed.
Figure 53:
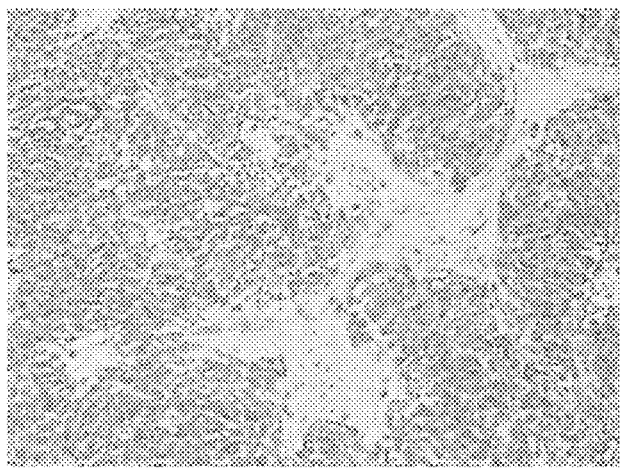
FIG. 53 shows a black and white version of an example of a cocktail of Tyrosinase+MART-1 staining a case of melanoma.
Figure 54:
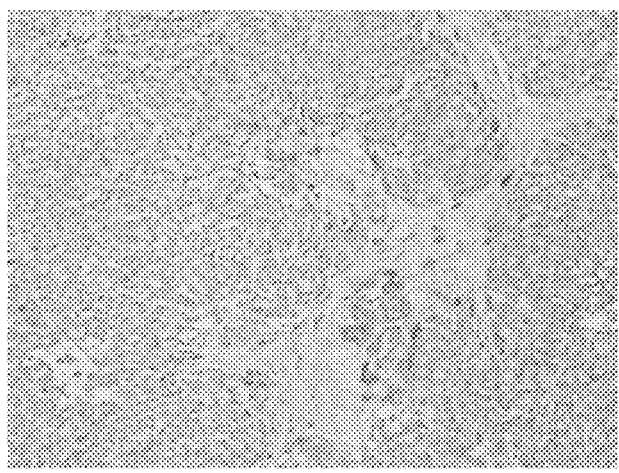
FIG. 54 shows a black and white version of the same case of melanoma shown in FIG. 53 stained with BC34. Perhaps reduced staining or no staining may be present.

Some cases of melanoma may stain with BC34 (FIG. 51), but perhaps not with Tyrosinase+MART-1 (FIG. 52). Other cases of melanoma may stain with Tyrosinase+MART-1 (FIG. 53), but perhaps not with BC34 (FIG. 54).

Figure 55:
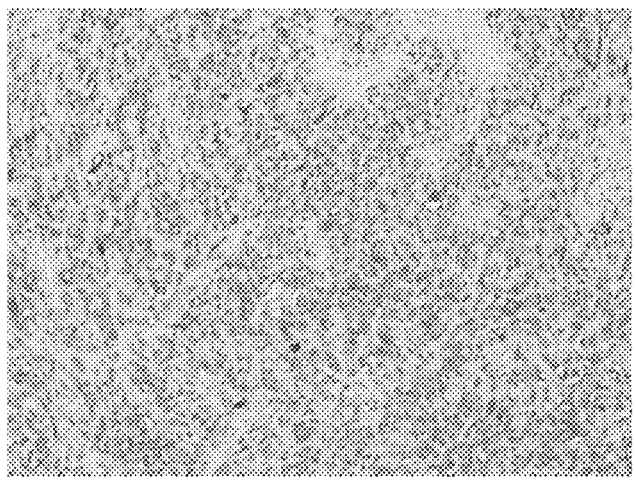
FIG. 55 shows a black and white version of an example of SOX10 [BC34]+Tyrosinase+MART-1 staining a case of melanoma.
Figure 56:
FIG. 56 shows a black and white version of the same case of melanoma shown in FIG. 51 stained with S100. Perhaps reduced staining or no staining may be present.

The cocktail of SOX10 [BC34]+Tyrosinase+MART-1 may stain cases of melanoma that are perhaps not stained with S100 (FIGS. 55, 56). In this way, the cocktail of SOX10 [BC34]+Tyrosinase+MART-1 may be more sensitive than S100.

Figure 57:
FIG. 57 shows a black and white version of an example of lymph node stained with an antibody cocktail of SOX10 [BC34]+Tyrosinase+MART-1. Perhaps reduced staining or no staining may be present.
Figure 59:
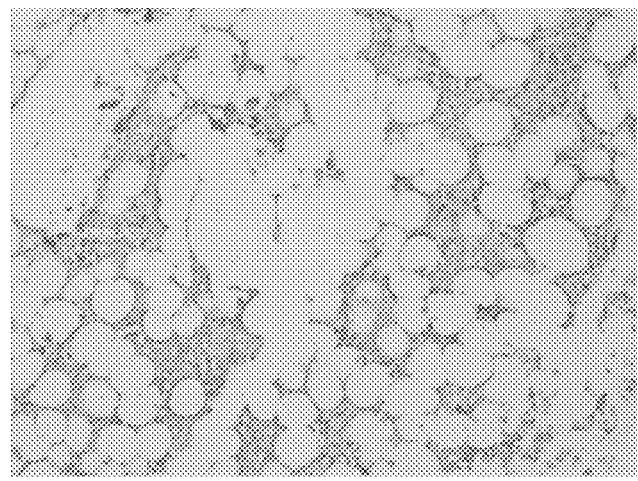
FIG. 59 shows a black and white version of an example of bone marrow stained with an antibody cocktail of SOX10 [BC34]+Tyrosinase+MART-1. Perhaps reduced staining or no staining may be present.
Figure 60:
FIG. 60 shows a black and white version of an example of staining with S100 in the same case of lymph node as shown in FIG. 57.

The cocktail of SOX10 [BC34]+Tyrosinase+MART-1 may also be more specific than 5100. SOX10 [BC34]+Tyrosinase+MART-1 does not stain lymph node, brain, or bone marrow (FIG. 57 59). One disadvantage of S100 is staining observed in tissues other than melanoma, including normal lymph node, brain, and bone marrow (FIG. 60, 62). Lymph node, brain and bone marrow may be common site for melanoma metastasis. Staining of S100 in these normal tissues may make diagnosis difficult, particularly when a pathologist is attempting to identify a small metastasis, or perhaps even result in an incorrect diagnosis.

Anti-SOX10 antibody [BC34] was evaluated by IHC on a variety of normal and neoplastic tissues. Typically, a cut-off of ≥about 5% of tumor cells staining was employed as the criteria to determine a case as "positive" for SOX10, and conversely <about 5% of tumor cells staining as the criteria to determine a case "negative."

In normal tissues (n=34), BC34 stained skin melanocytes, myoepithelial cells in breast and salivary gland, peripheral nerves, and brain (Table 3). BC34 also stained argentaffin cells throughout the digestive tract. BC34 stained 200/219 (91.3%) melanomas (Table 4). Notably, 23/24 (95.8%) spindle cell and desmoplastic melanomas were positive for SOX10. In addition, there was 100% staining for schwannomas and nevi.

In neoplasms tested (n=587), SOX10 was expressed in 18/109 (16.5%) infiltrating ductal breast cancers, and in none of the following (n=426) other carcinomas, including lung, colon, prostate, bladder, kidney, liver, esophagus, ovary, thyroid, adrenal, and testicular seminoma (Table 5). SOX10 was positive in 2/21 rhabdomyosarocomas, in 1/21 of leiomyosarcomas, and in 35% of CNS gliomas. Carcinoid tumors in the digestive tract and in the lung were all negative, except for staining of sustentacular cells.

Figure 49:
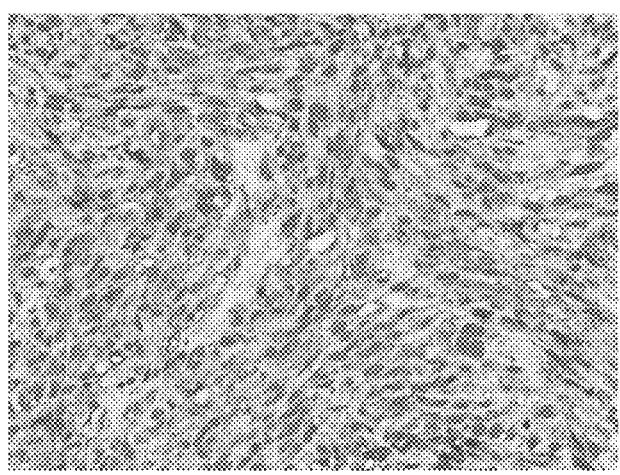
FIG. 49 shows a black and white version of a first example of an antibody cocktail of SOX10+Tyrosinase+MART-1 staining cases of melanoma.
Figure 50:
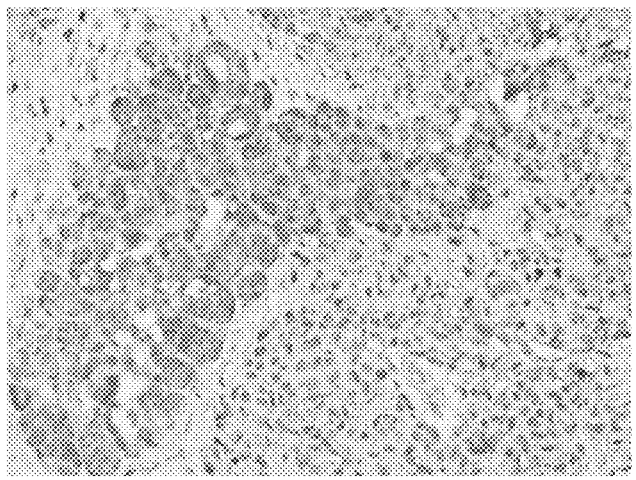
FIG. 50 shows a black and white version of a second example of an antibody cocktail of SOX10+Tyrosinase+MART-1 staining cases of melanoma.
Figure 58:
FIG. 58 shows a black and white version of an example of brain stained with an antibody cocktail of SOX10 [BC34]+Tyrosinase+MART-1. Perhaps reduced staining or no staining may be present.
Figure 61:
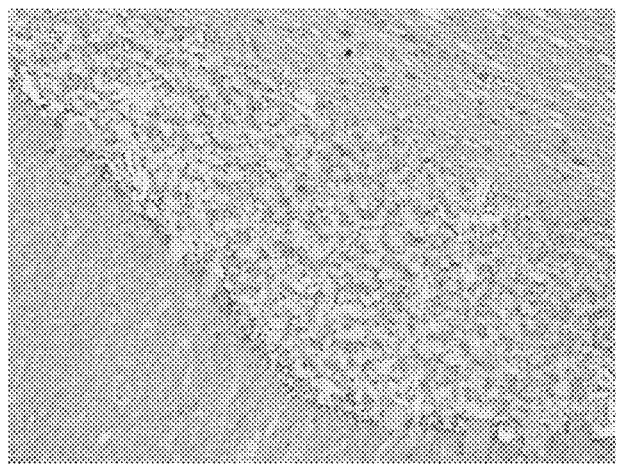
FIG. 61 shows a black and white version of an example of staining with S100 in the same case of brain as shown in FIG. 58.
Figure 62:
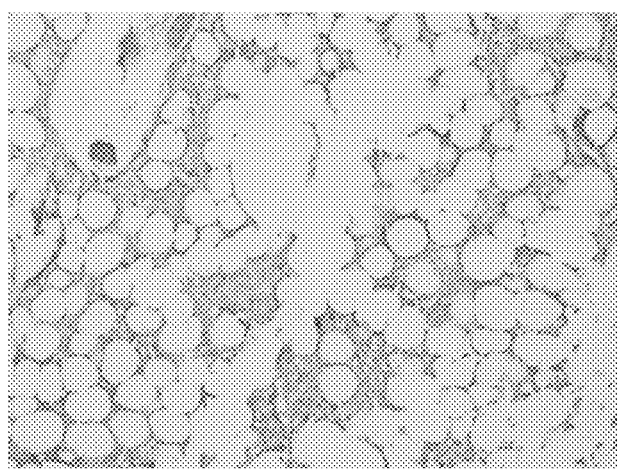
FIG. 62 shows a black and white version of an example of staining with S100 in the same case of bone marrow as shown in FIG. 59.

In melanomas, a cocktail of SOX10, Tyrosinase and MART-1 may be more sensitive than SOX10 alone, S100 alone, or even the cocktail of Tyrosinase+MART-1 (Table 6). Staining of Tyrosinase and MART-1 may be cytoplasmic (FIG. 47) and staining of SOX10 may be nuclear (FIG. 48). The cocktail of SOX10+Tyrosinase+MART-1 may show a combination of nuclear staining (SOX10) and cytoplasmic staining (MART-1 and Tyrosinase) (FIGS. 49-50). In some cases, SOX10 may be positive and Tyrosinase+MART-1 may be negative (FIG. 51, 52), or vice versa (FIG. 53, 54). The cocktail of SOX10+Tyrosinase+MART-1 may be positive in cases where S100 is negative (FIG. 55, 56). One case was found to be perhaps positive for 5100 and negative for SOX10+Tyrosinase+MART-1. SOX10 [BC34] may also be negative in lymph node, brain and bone marrow (FIG. 57-59), whereas 5100 may stain these tissues (FIG. 60-62).

TABLE 3

Normal Tissues Types (n = 34)

| Organ | SOX10 (+) | Organ | SOX10 (+) |
|---|---|---|---|
| Cerebrum | + | Stomach* | − |
| Cerebellum | + | Small intestine* | − |
| Adrenal | − | Colon* | − |
| Ovary | − | Liver | − |
| Pancreas* | − | Salivary gland | + |
| Thyroid | − | Kidney | − |
| Parathyroid* | − | Prostate | − |
| Testis | − | Uterus | − |
| Bone | − | Uterine cervix | − |
| Spleen | − | Striated muscle | − |
| Tonsil | − | Skin | + |
| Thymus | − | Nerve (peripheral) | + |
| Bone marrow | − | Lung | − |
| Lung | − | Larynx | − |
| Cardiac | − | Bladder | − |
| Esophagus | − | Placenta | − |
| Pituitary | − | Mesothelium | − |

*A few argentaffin cells throughout the digestive tract and/or a few/sparse neuroendocrine type cells were stained for SOX10.

TABLE 4

Melanoma

| Melanoma | Cases | SOX10 (+) | % (+) |
|---|---|---|---|
| Melanoma (skin) | 109 | 105 | 96 |
| Metastatic Melanoma | 86 | 72 | 83.7 |
| Spindle cell melanoma | 9 | 9 | 100 |
| Desmoplastic melanoma | 13 | 12 | 92.3 |
| Desmoplastic/Spindle cell mixed features | 2 | 2 | 100 |
| Epithelioid melanoma | 2 | 2 | 100 |
| Sarcomatoid melanoma | 2 | 2 | 100 |
| Plasmacytoid melanoma | 2 | 2 | 100 |
| Balloon cell melanoma | 2 | 2 | 100 |
| Rhabdoid melanoma | 1 | 1 | 100 |
| Schwannoma (neurilemmoma) | 28 | 28 | 100 |
| Nevus | 20 | 20 | 100 |

TABLE 5

Various Neoplastic Tissues (n = 587)

| Cancers | # of Cases | SOX10 + | % (+) |
|---|---|---|---|
| Lung | 178 | 0 | 0 |
| Colon | 24 | 0 | 0 |
| Breast | 109 | 18 | 16.5 |
| Prostate | 13 | 0 | 0 |
| Bladder | 48 | 0 | 0 |
| Kidney | 15 | 0 | 0 |
| Liver | 57 | 0 | 0 |
| Esophagus | 10 | 0 | 0 |
| Seminoma | 17 | 0 | 0 |
| Ovarian | 12 | 0 | 0 |
| Adrenal gland | 10 | 0 | 0 |
| Thyroid (papillary) | 4 | 0 | 0 |
| Leiomyosarcoma | 21 | 2 | 9.5 |
| Rhabdomyosarcoma | 21 | 1 | 4.8 |
| Brain | 29* | 51 | 57 |
| Pancreas | 14 | 0 | 14 |
| Lymphoma | 5 | 0 | 0 |
| Carcinoids | 8 | 0** | 0 |
| Cervix | 11 | 0 | 0 |

*SOX10 was expressed primarily in astrocytoma (24/39), and in limited cases of glioblastoma, medulloblastoma, and malignant ependymoma.
**(≤1%)

TABLE 6

Comparison of SOX10, S100, Tyrosinase + MART-1,
and Tyrosinase + MART-1 + SOX10

| Antibody or Antibody Cocktail | Melanoma Positive Cases/Total Cases (% positive) |
|---|---|
| S100 | 60/80 (75%) |
| SOX10 | 64/80 (80%) |
| Tyrosinase + MART-1 | 71/80 (89%) |
| SOX10 + Tyrosinase + MART-1 | 73/80 (91%) |

These examples demonstrate the advantages of BC34 and perhaps show that BC34 has several advantages over known antibodies, including superior sensitivity or specificity, possibly resulting in cleaner staining patterns, with less background or undesirable cytoplasmic staining.

In some embodiments of the present invention, anti-SOX10 antibodies such as the mouse monoclonal anti-SOX10 antibody BC34 may be suitable for use in many variations of the above protocols and other methods known to those in the art. Specimens stained with BC34 may be archived using a permanent mounting media and a coverslip. The antibody BC34 may also be used in an automated staining instrument, using standard protocols. One can also envision the use of many alternative detection methods (e.g., fluorescence), detection enzymes (e.g., alkaline phosphatase (AP), beta-galactosidase, or the like), and perhaps even chromogens (e.g., 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide, or the like), generally known to those in the art.

An epitope of an anti-SOX10 antibody such as mouse monoclonal anti-SOX10 antibody BC34, or a portion thereof, may be a useful antigen for the production of new monoclonal antibodies, including production in species other than mouse (e.g. rabbit, goat, horse, chicken, etc.) as one skilled in the art would understand. In fact, the particular epitope of BC34 may be one of the features that contributes to its advantageous properties.

While the use of anti-SOX10 antibodies such as BC34 in immunohistochemistry of formalin-fixed paraffin embedded tissues may be described here, its utility in other immunoassays may be readily envisioned and are meant to be included in this application. In particular, it may be well known that many of the same reagents used in IHC of FFPE may also be used in IHC of frozen-tissue sections. Anti-SOX10 antibodies such as BC34 may also be useful in other immunoassays, including ELISA, perhaps using generally known methods.

In another aspect of the invention, perhaps related to IHC, an anti-SOX10 antibody may be used in conjunction with one or more additional primary antibodies as part of a cocktail, to perform a "double-stain" procedure (also described as multi-stain or even multiplex). Such "double-stain" procedures may be generally well known in the art; however, the best combinations of primary antibodies for a particular diagnostic application may not be known.

In this method, anti-SOX10 antibodies such as a mouse monoclonal anti-SOX10 antibody BC34 could be combined with one or more antibodies in a single primary antibody cocktail, perhaps suitable for simultaneous application to a specimen. The antibodies may be derived from a mouse host or a rabbit host or the like. The antibodies may be monoclonal or polyclonal. In embodiments, an antibody cocktail may be used in a double-stain IHC procedure to produce two or more colored stains that may identify the presence or absence of target protein antigens in the tissue specimen. For example, in embodiments where an antibody cocktail may be comprised of mouse and rabbit antibodies, a detection system may include an anti-mouse antibody conjugated to horseradish peroxidase (HRP) and perhaps even an anti-rabbit antibody conjugated to alkaline phosphatase (AP) may be used to produce the two-color stain. 3,3'-diaminobenzidine (DAB) may be used to produce a brown stain, perhaps facilitated by HRP, and it may identify the presence or absence, and/or location, of mouse antibodies bound in the specimen; Fast Red may be used to produce a fuchsia/red stain, perhaps facilitated by AP, and it may identify the presence or absence, and/or location, of rabbit antibodies in the specimen. In other embodiments, a detection system may include an anti-mouse antibody conjugated to AP and an anti-rabbit antibody conjugated to HRP which may be used to produce a two-color stain that may identify the presence or absence, and/or location of the mouse antibodies with a red stain and the rabbit antibodies with a brown stain, perhaps when Fast Red and DAB may be used as chromogens. In some embodiments, an anti-mouse antibody conjugated to HRP and perhaps an anti-rabbit antibody conjugated to AP may be applied to the specimen as a cocktail, in a single solution, or they may be applied in separate, sequential steps.

The anti-mouse or anti-rabbit antibodies comprising the antibody-enzyme conjugates may be derived from a different host species, including, but not limited to mouse, rabbit, chicken, horse, rat, goat, sheep, or the like. A primary antibody may be from a variety of host species, including, but not limited to mouse, rabbit, chicken, horse, rat, goat, sheep, or the like. In embodiments, an antibody may include an antibody-enzyme conjugate and a primary antibody could be obtained from two different host species. Chromogens other than DAB and/or Fast Red may be used as well.

Multiple alternatives to a double-staining method are possible, including but not limited to the use of more than two antibodies, the use of species other than mouse and rabbit, other chromogens and detection systems, a different order of detection steps, and perhaps even modifications resulting in three or more colors (which may require a denaturing step).

In some embodiments, a single color stain may be used for a primary antibody cocktail. In one example, if the primary antibody cocktail is comprised of antibodies all derived from the same host species, then a single detection system may be used to stain for the presence of all of the antibodies with a single color. The presence or absence of each antibody may be determined based on cellular localization, or perhaps such determination is not necessary and the staining may be interpreted effectively without identifying the presence or absence of each antibody. For example, mouse monoclonal anti-SOX10 antibody BC34 may be combined with mouse monoclonal anti-MART1 in a primary antibody cocktail and used in an IHC procedure with anti-mouse conjugated HRP detection and DAB for visualization, to produce a brown stain. In another aspect, a primary antibody cocktail comprised of two or more antibodies from different host species may be used in a similar manner to produce a single color stain. For example, mouse monoclonal anti-SOX10 BC34 may be combined with rabbit polyclonal anti-S100 antibody and used in an IHC procedure with anti-mouse conjugated HRP and anti-rabbit conjugated HRP, and DAB for visualization, to produce a brown stain.

Certain steps of an IHC procedure may be performed sequentially or simultaneously, perhaps by using a cocktail of reagents, as known to those skilled in the art. For example, antibodies described in a primary antibody cocktail may alternatively be applied in sequential steps of one or more antibodies. Similarly, detection reagents may be applied simultaneously in reagent cocktail or separate reagents in sequential steps.

Antibodies that may be useful for diagnosis when combined with an anti-SOX10 antibody such as a mouse monoclonal anti-SOX10 antibody BC34 in a primary antibody cocktail for use in multi-stain procedures include:

| Antibody Combination and (Host Species) | Possible Staining Pattern (cellular localization, stain color*) | Possible Diagnostic Utility |
|---|---|---|
| SOX10 [BC34] (Mouse) S100 (Rabbit) | SOX10 (Nuclear, Brown) S100 (Cytoplasmic and Nuclear, Red) | SOX10 staining may be observed in melanoma; S100 staining may be observed in melanoma |

*The listed color of each stain may be a result of a detection system that may include an anti-mouse antibody perhaps conjugated to HRP and even an anti-rabbit antibody perhaps conjugated to AP, perhaps even with DAB and Fast Red as chromogens, which may result in brown staining for mouse antibodies and red staining for rabbit antibodies. Alternatively, the detection system may include an anti-mouse antibody perhaps conjugated to AP and even an anti-rabbit antibody perhaps conjugated to HRP, perhaps even with DAB and Fast Red as chromogens, which may result in red staining for mouse antibodies and brown staining for rabbit antibodies. Other color combinations may be obtained using other detection systems or chromogens and all are meant to be included in this disclosure.

In some embodiments, reagents may be applied sequentially in a fashion to produce a double stain, even perhaps when using antibodies from the same host species. For example, mouse monoclonal BC34 could be applied, followed by perhaps anti-mouse-HRP detection and DAB chromogen steps. After a denaturing step, perhaps using an acidic solution, a second mouse monoclonal antibody may be applied, perhaps a mouse monoclonal anti-nestin antibody or a mouse monoclonal anti-MART1 antibody, followed by perhaps anti-mouse-AP detection and Fast Red chromogen steps, to product a two color stain.

In some embodiments, a cocktail of antibodies derived from the same host species may be used, resulting in a single color stain. For example, a cocktail of mouse monoclonal SOX10 [BC34], mouse monoclonal Tyrosinase [T311], and mouse monoclonals MART-1 [M2-7C10] and [M2-9E3] may be applied and detected by anti-mouse-HRP and DAB, or perhaps anti-mouse-AP and Fast Red. Other embodiments may include an antibody cocktail of SOX10 and Tyrosinase, or perhaps SOX10 and MART-1. Mouse monoclonal SOX10 may also be combined with rabbit polyclonal or monoclonal antibodies of Tyrosinase or MART-1 in any of the combinations described above, perhaps even in a double stain procedure. Antibody cocktails of SOX10, Tyrosinase and/or MART-1 may be superior to other potential markers of melanoma, including perhaps S100. SOX10, Tyrosinase and MART-1 may be more sensitive than S100 in melanoma, perhaps because SOX10 may stain desmoplastic melanoma and spindle cell melanoma and S100 may not stain these types. SOX10, Tyrosinase and MART-1 may also be more specific than S100, as they may not stain brain, lymph node or bone marrow, common sites for melanoma metastases, in the way that S100 does, perhaps aiding in the identification of micro-metastases in these sites. In certain embodiments, clones other than those used in the examples (including other clones of SOX10 other than BC34) may be suitable and perhaps interchangeable, or perhaps even superior to the clones used in the examples.

In many embodiments, antibodies that bind cytokeratin markers may be used in different combinations, and in some cases, interchangeably, as known to those skilled in the art. For example, CK5 may perhaps be interchangeable with CK5/6 or CK5/14. Similarly, HMWCK (high molecular weight cytokeratin) may be used interchangeably with CK5/6 or CK5/14.

In many cases, diagnosis may often be performed on limited tissue samples from cytology or a biopsy, and it may be important to conserve tissue for further molecular testing; therefore, an efficient approach to diagnosis that consumes minimal tissue, but provides optimal specificity and/or sensitivity may be preferred. A method that provides useful diagnostic information, while consuming minimal tissue from the specimen, perhaps by use of an antibody cocktail, or conceivably by the feature of improved sensitivity or specificity, may be preferred.

An anti-SOX10 antibody such as a mouse monoclonal anti-SOX10 antibody BC34 may be specific for detection of SOX10 and may be useful in immunohistochemical procedures for diagnosis of several types of cancers in human tissue samples. In particular, anti-SOX10 antibody such as BC34 may have advantages over the RP anti-SOX10 antibody, including but not limited to greater sensitivity, more intense staining, greater specificity and cleaner staining, with perhaps less background staining, as well as perhaps a lack of staining of carcinoids and perhaps a lack of staining of lung adenocarcinoma.

Figure 2:
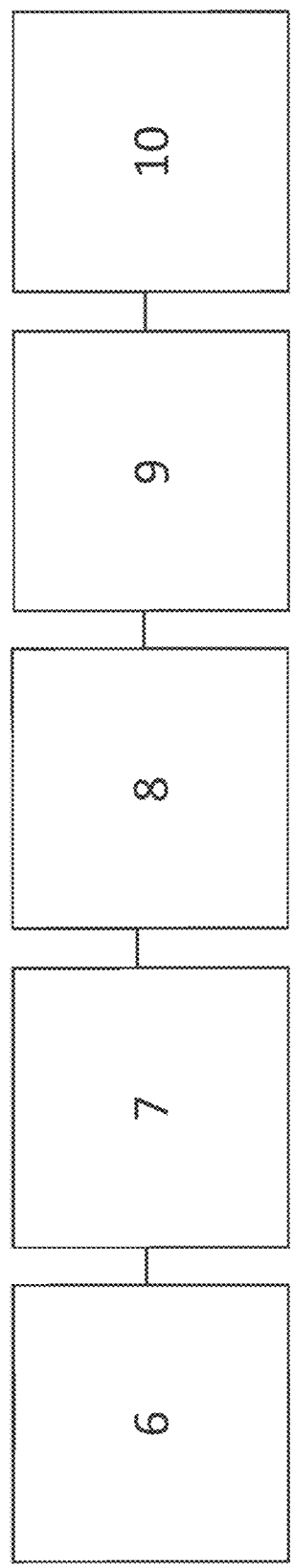
FIG. 2 shows an example of a schematic summary of an immunoassay method in accordance with various embodiments of the present invention.

As but one example of an immunoassay method, embodiments of the present invention may provide obtaining tissue from an animal or human to be tested (6), fixing or freezing said tissue (7), treating said fixed or frozen tissue to unmask epitopes to SOX10 (8), contacting said treated tissue with an antibody or fragment thereof as discussed herein in an amount and under conditions such that an antibody or fragment thereof binds to a SOX10 protein if the protein is present in said tissue (9); and perhaps even detecting the presences of said bound antibodies (10), as schematically represented in FIG. 2.

FIG. 1 shows a schematic summary of various embodiments of the present invention including a kit (5) which may provide an antibody, fragment thereof, portion thereof, in a composition or even in a cocktail, perhaps even provided from a hybridoma, the antibody (1) or the like may be contacted with a biological sample (2) to form at least one antibody-antigen complex (3) which may then be detected with a detector (4).

The present invention may provide, in embodiments, a diagnostic or even prognostic test kit which may include an antibody or fragment thereof (as discussed herein) with an antibody detection element of the antibody or fragment thereof perhaps when bound to an antigen. This may provide a method of contacting a biological sample with an antibody or fragment thereof and even detecting binding of, or even the presence of the antibody or fragment thereof bound to a protein or with an antigen in the biological sample perhaps using an antibody detection element. Embodiments may provide an immunoassay method for detect a SOX10 protein in a mammal or human perhaps by obtaining a tissue from an animal or a human to be tested, contacting the tissue with an antibody or fragment thereof in accordance with the various embodiments presented herein perhaps in an amount and under conditions such that the antibody or fragment thereof may bind to a SOX10 protein if the protein is present in the tissue; and even detecting the presence of bound antibodies. A biological sample may include but is not limited to blood, urine, urothelial tissue, transitional cell tissue, bladder tissue, normal tissue, neoplastic tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue, breast tissue, or the like perhaps depending on the antibody or even cocktail being used.

It is noted that use of terms such as SOX10, SOX10 antibody, BC34, or the like may relate to anti-SOX10 antibodies or the like as appropriate as one skilled in the art would understand. It is noted that the components of an antibody cocktail may be denoted with a "+". (e.g. "MART-1+Tyrosinase" identifies a cocktail of MART-1 and Tyrosinase antibodies.) Also, in some cases an antibody reagent may include more than one antibody clone to the same target (e.g. MART-1 may include two anti-MART-1 mouse monoclonal antibodies, clone M2-7C10 and clone M2-9E3).

The article, "A Newly Developed Mouse Monoclonal SOX10 Antibody is a Highly Sensitive and Specific Marker for Malignant Melanoma, Including Spindle Cell and Desmoplastic Melanomas" by Tacha, David; Qi, Weiman; Bremer, Ryan; Yu Charlie; Hoang, Laura; Ra, Seong; and Robbins, Bruce. Biocare Medical, Concord, Calif., San Diego Pathologists Medical Group, San Diego, Calif., has been attached to this application and is hereby incorporated by reference in its entirety herein.

As can be easily understood from the foregoing, the basic concepts of the present invention may be embodied in a variety of ways. It involves both antibody techniques as well as devices to accomplish the appropriate antibody. In this application, the antibody techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detection" or "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any law, statutes, regulations, or rules mentioned in this application for patent; or patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

I. U.S. PATENT DOCUMENTS

| Patent Number | Kind Code | Issue Date | Name of Patentee or Applicant of cited Document |
|---|---|---|---|
| 7,468,425 | B2 | 2008 Dec. 23 | Sidransky, et al. |
| 6,946,256 | B1 | 2005 Sep. 20 | McKeon, et al. |

II. FOREIGN PATENT DOCUMENTS

| Foreign Document Number | Country Code | Kind Code | Publication Date | Name |
|---|---|---|---|---|
| 2012154983 | WO | A2 | 2012 Nov. 15 | Biocare Medical, LLC |

III. NON-PATENT LITERATURE DOCUMENTS

"SOX10 expression in malignant melanoma, carcinoma, and normal tissues." Mohamed A, Gonzalez R S, Lawson D, Wang J, Cohen C. *Appl Immunohistochem Mol Morphol.* 2012; Ahead of Epub "The SOX10/Sox10 gene from human and mouse: sequence, expression, and transactivation by the encoded HMG domain transcription factor." Pusch C, Hustert E, Pfeifer D, et. al. *Hum Genet.* 1998; 103: 115-123

"The importance of having your SOX on: role of SOX10 in the development of neural crest-derived melanocytes and glia." Mollaaghababa R, Pavan W J. *Oncogene.* 2003; 22: 3024-3034

"Expression of the SOX10 gene during human development." Bondurand N, Kobetz A, Pingault V, et. al. *FEBS Lett.* 1998; 432: 168-172

"Oligodendroglial-specific transcriptional factor SOX10 is ubiquitously expressed in human gliomas." Bannykh S I, Stolt C C, Kim J, Perry A, Wegner M. *J Neurooncol.* 2006 January; 76(2): 115-27

"The transcription factor Sox10 is a key regulator of peripheral glial development." Britsch S, Goerich D E, Riethmacher D, et. al. *Genes Dev.* 2001; 15: 66-78

"Oligodendroglial-specific transcriptional factor SOX10 is ubiquitously expressed in human gliomas." Bannykh SI, Stolt C C, Kim J, Perry A, Wegner M. *J Neurooncol.* 2006 January; 76(2): 115-27

"Incidence and survival of desmoplastic melanoma in the United States, 1992-2007." Feng Z, Wu X, Chen V, et. al. *J Cutan Pathol.* 2011; 38: 616-624

Desmoplastic malignant melanoma." Conley J, Lattes R, Orr W. *Cancer.* 1971; 28: 914-916

"Desmoplasia and neurotropism. Prognostic variables in patients with stage I melanoma." Baer S C, Schultz D, Synnestvedt M, et. al. *Cancer.* 1995; 76: 2242-2247

"Subclassification of desmoplastic melanoma: pure and mixed variants have significantly different capacities for lymph node metastasis." George E, McClain S E, Slingluff C L, et. al. *J Cutan Pathol.* 2009; 36: 425-432

"SOX10 expression distinguishes desmoplastic melanoma from its histologic mimics." Palla B, Su A, Binder S, Dry S. *Am J Dermatopathol.* 2013 July; 35(5): 576-81

"Sox10 is expressed in primary melanocytic neoplasms of various histologies, but not in fibrohistiocytic proliferations and histiocytoses." Shin J, Vincent J G, Cuda J D, et. al. *J Am Acad Dermatol.* 2012 October; 67(4): 717-26

"MCW melanoma cocktail for the evaluation of micrometastases in sentinel lymph nodes of cutaneous melanoma." Shidham V B, Chang C C. *Expert Rev Mol Diagn.* 2005 May; 5(3): 281-90

"Microphthalmia transcription factor in the immunohistochemical diagnosis of metastatic melanoma: comparison with four other melanoma markers." Miettinen M, Fernandez M, Franssila K, et al. *Am J Surg Pathol.* 2001 February; 25(2): 205-11

"Sox10: a pan-schwannian and melanocytic marker." Nonaka D, Chiriboga L, Rubin B P. *Am J Surg Pathol.* 2008; 32: 1291-1298

"Neural crest transcription factor Sox10 is preferentially expressed in triple-negative and metaplastic breast carcinomas." Cimino-Mathews A, Subhawong A P, Elwood H, et. al. *Hum Pathol.* 2013 June; 44(6): 959-65

"Sox10-positive sustentacular cells in neuroendocrine carcinoma of the lung." Tsuta K, Raso M G, Kalhor N, et. al. *Histopathology.* 2011 January; 58(2): 276-85

"SOX10 and S100 in the diagnosis of soft-tissue neoplasms." Karamchandani J R, Nielsen T O, van de Rijn M, West R B. *Appl Immunohistochem Mol Morphol.* 2012 October; 20(5): 445-50

U.S. Provisional Application No. 61/706,312 filed Sep. 27, 2012; entitled Systems and Methods for Anti-Uroplakin II Antibodies U.S. Nonprovisional Application No. 13/830,473 filed Mar. 14, 2013; entitled Systems and Methods for Anti-Uroplakin III Antibodies International Application Number PCT/US2013/062043m filed Sep. 26, 2013; Entitled Anti-Uroplakin II Antibodies Systems and Methods Nonaka D, Chiriboga L, Rubin B P. Sox10: a pan-schwannian and melanocytic marker. Am J Surg Pathol. 2008; 32: 1291-1298

Karamchandani J R, et. al. SOX10 and S100 in the diagnosis of soft-tissue neoplasms. Appl Immunohistochem Mol Morphol. 2012 October; 20(5): 445-50

Buonaccorsi J N, Prieto V G, Torres-Cabala C, Suster S, Plaza J A. Diagnostic Utility and Comparative Immunohistochemical Analysis of MITF-1 and SOX10 to Distinguish Melanoma In Situ and Actinic Keratosis: A Clinicopathological and Immunohistochemical Study of 70 Cases. Am J Dermatopathol. 2013 Jun. 18. [Epub ahead of print]

| |
|---|
| Agnarsdottir M, Sooman L, Bolander A, et. al. SOX10 expression in superficial spreading and nodular malignant melanomas. Melanoma Res. 2010 December; 20(6): 468-78 |
| Seong I, Min H J, Lee J H, et. al. Sox10 controls migration of B16F10 melanoma cells through multiple regulatory target genes. PLoS One. 2012 ;7(2) |
| Ramos-Herberth F I, Karamchandani J, Kim J, Dadras S S. SOX10 immunostaining distinguishes desmoplastic melanoma from excision scar. J Cutan Pathol. 2010 September; 37(9): 944-52 |
| Ivanov S V, Panaccione A, Nonaka D, et. al. Diagnostic SOX10 gene signatures in salivary adenoid cystic and breast basal-like carcinomas. Br J Cancer. 2013 Jul 23; 109(2): 444-51 |
| U.S. Provisional Application No. 61/886,448 filed Oct. 3, 2013; entitled Systems and Methods for Anti-SOX10 Antibodies |
| U.S. Provisional Application No. 61/941,907 filed Feb. 19, 2014; entitled Systems and Methods for Anti-SOX10 Antibodies |
| Shidham, et al., MCW melanoma cocktail for the evaluation of micrometastases in sentinel lymph nodes of cutaneous melanoma; expert Rev Mol Diagn. 2005 May; 5(3): 281-90 |
| Miettinin M, Fernandez M, Franssila K, et al. Am J Surge Pathol. 2001 February; 25(2): 205-11; Microphthalmia transcription factor in the immunohistochemical diagnosis of metastatic melanoma: comparison with four other melanoma markers |

Thus, the applicant(s) should be understood to have support to claim and make a statement of invention to at least: i) each of the antibody devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An antibody produced by the hybridoma deposited with the American Type Culture Collection (ATCC) under ATCC Patent Deposit Designation No. PTA-120969.

2. A composition comprising the antibody of claim 1 and at least one additional antibody or fragment thereof.

3. The composition of claim 2, wherein the at least one additional antibody or fragment thereof is derived from a different species than the antibody of claim 1.

4. The composition of claim 2, wherein the at least one additional antibody or fragment thereof is derived from a species selected from the group consisting of rabbit, goat, horse, chicken, and human.

5. The composition of claim 2, wherein the at least one additional antibody or fragment thereof binds specifically to a protein selected from the group consisting of Tyrosinase, melanoma antigen recognized by T cells 1 (MART-1), and S100.

6. The composition of claim 2, further comprising a label attached to at least one of the antibody of claim 1 and the at least one additional antibody or fragment thereof.

7. The composition of claim 2, wherein said label is selected from the group consisting of a radioactive element, magnetic particles, radioisotope, fluorescent dye, enzyme, toxin, signal, stain, detection enzymes, horseradish peroxidase (HRP), alkaline phosphatase (AP), beta-galactosidase, chromogens, 3,3'-diaminobenzidine, 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide, and any combination thereof.

8. A method for detecting, in a biological sample, a protein to which the antibody of claim 1 binds; comprising the steps of contacting the biological sample with the antibody of claim 1 and detecting the presence of the antibody bound to the protein in the biological sample.

9. The method of claim 8, wherein said biological sample comprises lung tissue, bladder tissue, breast tissue, or prostate tissue.

10. The method of claim 8, wherein said biological sample is selected from the group consisting of a normal tissue, neoplastic tissue, bladder tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue, skin tissue, and breast tissue.

11. The method of claim 8, wherein said detecting said presence of the antibody bound to the protein is performed on an automated staining device.

12. The method of claim 8, wherein said detecting said presence of the antibody bound to the protein comprises detecting selected from the group consisting of: manually detecting, automatically detecting, and image analysis.

13. The method of claim 8, wherein said detecting comprises a method selected from the group consisting of immunohistochemistry (IHC), IHC of formalin-fixed paraffin embedded (FFPE) tissue, IHC of frozen-tissue sections, immunocytochemistry, and ELISA.

14. The method of claim 8, wherein the biological sample comprises tissue; and wherein the method further comprises the steps of fixing or freezing said tissue, and treating said fixed or frozen tissue to unmask epitopes to Sry-related HMG-Box gene 10 protein (SOX10).

* * * * *

SEQUENCE LISTING

```
<160> NUMBER OF SEQ ID NOS: 35

<210> SEQ ID NO 1
<211> LENGTH: 366
<212> TYPE: DNA
<213> ORGANISM: Mus musculus

<400> SEQUENCE: 1
caggttactc tgaaagagtc tggccctggg atattgcagc cctcccagac cctcagtctg      60
acttgttctt tctctgggtt ttcactgagt acttttctta taggagtagg ctggattcgt     120
cagccttcag ggaagggtct ggagtggctg gcacacattt ggtggaatga taataagtac     180
tataatacag ccctgaagaa ccggctcaca atctccaagg atacctccaa caatcaggta     240
ttcctcaaga tcgccagtgt ggacactaca gatactgcca catactactg tgttcgaatg     300
gcagggatag gtgggacgga tgctatggac tactggggtc aaggaacctc agtcaccgtc     360
tcctca                                                                 366

<210> SEQ ID NO 2
<211> LENGTH: 334
<212> TYPE: DNA
<213> ORGANISM: Mus musculus

<400> SEQUENCE: 2
gacattgtgc tcacccaatc tccagcttct ttggctgtgt ctctagggca gagagccacc      60
atctcctgca gagccagtga aattgttgaa tattatggca caaatttact gcagtggtac     120
caacagaaac caggtcagcc acccaaactc ctcatctatg ctgcatccaa cgtagaatct     180
ggggtccctg ccaggtttag tggcagtggg tctgggacag acttcagcct caacatccat     240
cctgtggagg aggatgatat tgcaatatat ttctgtcagc aaagtaggaa ggttccgtgg     300
acgttcggtg gaggcaccaa gctggaaatc aaac                                 334

<210> SEQ ID NO 3
<211> LENGTH: 15
<212> TYPE: PRT
<213> ORGANISM: Homo sapiens

<400> SEQUENCE: 3

Gln Gly Gly Thr Ala Ala Ile Gln Ala His Tyr Lys Ser Ala His
1               5                   10                  15

<210> SEQ ID NO 4
<211> LENGTH: 122
<212> TYPE: PRT
<213> ORGANISM: Mus musculus

<400> SEQUENCE: 4

Gln Val Thr Leu Lys Glu Ser Gly Pro Gly Ile Leu Gln Pro Ser Gln
```

```
                1               5                   10                  15
            Thr Leu Ser Leu Thr Cys Ser Phe Ser Gly Phe Ser Leu Ser Thr Phe
                                20                  25                  30

Leu Ile Gly Val Gly Trp Ile Arg Gln Pro Ser Gly Lys Gly Leu Glu
                            35                  40                  45

Trp Leu Ala His Ile Trp Trp Asn Asp Asn Lys Tyr Tyr Asn Thr Ala
                        50                  55                  60

Leu Lys Asn Arg Leu Thr Ile Ser Lys Asp Thr Ser Asn Asn Gln Val
             65                 70                  75                  80

Phe Leu Lys Ile Ala Ser Val Asp Thr Thr Asp Thr Ala Thr Tyr Tyr
                                85                  90                  95

Cys Val Arg Met Ala Gly Ile Gly Gly Thr Asp Ala Met Asp Tyr Trp
                            100                 105                 110

Gly Gln Gly Thr Ser Val Thr Val Ser Ser
                        115                 120
```

<210> SEQ ID NO 5
<211> LENGTH: 111
<212> TYPE: PRT
<213> ORGANISM: Mus musculus

<400> SEQUENCE: 5

```
            Asp Ile Val Leu Thr Gln Ser Pro Ala Ser Leu Ala Val Ser Leu Gly
             1               5                   10                  15

Gln Arg Ala Thr Ile Ser Cys Arg Ala Ser Glu Ile Val Glu Tyr Tyr
                                20                  25                  30

Gly Thr Asn Leu Leu Gln Trp Tyr Gln Gln Lys Pro Gly Gln Pro Pro
                            35                  40                  45

Lys Leu Leu Ile Tyr Ala Ala Ser Asn Val Glu Ser Gly Val Pro Ala
                        50                  55                  60

Arg Phe Ser Gly Ser Gly Ser Gly Thr Asp Phe Ser Leu Asn Ile His
             65                 70                  75                  80

Pro Val Glu Glu Asp Asp Ile Ala Ile Tyr Phe Cys Gln Gln Ser Arg
                                85                  90                  95

Lys Val Pro Trp Thr Phe Gly Gly Gly Thr Lys Leu Glu Ile Lys
                            100                 105                 110
```

<210> SEQ ID NO 6
<211> LENGTH: 10
<212> TYPE: PRT
<213> ORGANISM: Mus musculus

<400> SEQUENCE: 6

```
            Gly Phe Ser Leu Ser Thr Phe Leu Ile Gly
             1               5                   10
```

<210> SEQ ID NO 7
<211> LENGTH: 7
<212> TYPE: PRT
<213> ORGANISM: Mus musculus

<400> SEQUENCE: 7

```
            Ile Trp Trp Asn Asp Asn Lys
             1               5
```

<210> SEQ ID NO 8
<211> LENGTH: 14
<212> TYPE: PRT

```
<400> SEQUENCE: 8

Val Arg Met Ala Gly Ile Gly Gly Thr Asp Ala Met Asp Tyr
1               5                   10

<210> SEQ ID NO 9
<211> LENGTH: 10
<212> TYPE: PRT
<213> ORGANISM: Mus musculus

<400> SEQUENCE: 9

Glu Ile Val Glu Tyr Tyr Gly Thr Asn Leu
1               5                   10

<210> SEQ ID NO 10
<211> LENGTH: 3
<212> TYPE: PRT
<213> ORGANISM: Mus musculus

<400> SEQUENCE: 10

Ala Ala Ser
1

<210> SEQ ID NO 11
<211> LENGTH: 9
<212> TYPE: PRT
<213> ORGANISM: Mus musculus

<400> SEQUENCE: 11

Gln Gln Ser Arg Lys Val Pro Trp Thr
1               5

<210> SEQ ID NO 12
<211> LENGTH: 31
<212> TYPE: DNA
<213> ORGANISM: Mus musculus

<400> SEQUENCE: 12
gggaattcga ggtgcagctg caggagtctg g                              31

<210> SEQ ID NO 13
<211> LENGTH: 23
<212> TYPE: DNA
<213> ORGANISM: Mus musculus

<400> SEQUENCE: 13
ggaaggtgtg cacaccgctg gac                                       23

<210> SEQ ID NO 14
<211> LENGTH: 23
<212> TYPE: DNA
<213> ORGANISM: Mus musculus

<400> SEQUENCE: 14
ggaaggtgtg cacaccactg gac                                       23

<210> SEQ ID NO 15
<211> LENGTH: 23
<212> TYPE: DNA
<213> ORGANISM: Mus musculus

<400> SEQUENCE: 15
ggaaggtgtg cacactgctg gac                                       23
```

```
<210> SEQ ID NO 16
<211> LENGTH: 23
<212> TYPE: DNA
<213> ORGANISM: Mus musculus

<400> SEQUENCE: 16
agactgtgcg cacaccgctg gac                                    23

<210> SEQ ID NO 17
<211> LENGTH: 31
<212> TYPE: DNA
<213> ORGANISM: Mus musculus

<400> SEQUENCE: 17
gggaattcga ggtgcagctg caggagtctg g                           31

<210> SEQ ID NO 18
<211> LENGTH: 22
<212> TYPE: DNA
<213> ORGANISM: Mus musculus

<400> SEQUENCE: 18
gctcagggaa atagcccttg ac                                     22

<210> SEQ ID NO 19
<211> LENGTH: 22
<212> TYPE: DNA
<213> ORGANISM: Mus musculus

<400> SEQUENCE: 19
gctcagggaa ataaccottg ac                                     22

<210> SEQ ID NO 20
<211> LENGTH: 22
<212> TYPE: DNA
<213> ORGANISM: Mus musculus

<400> SEQUENCE: 20
actcagggaa gtagcccttg ac                                     22

<210> SEQ ID NO 21
<211> LENGTH: 22
<212> TYPE: DNA
<213> ORGANISM: Mus musculus

<400> SEQUENCE: 21
gctcagggaa gtagcctttg ac                                     22

<210> SEQ ID NO 22
<211> LENGTH: 21
<212> TYPE: DNA
<213> ORGANISM: Mus musculus

<400> SEQUENCE: 22
tgctgctgct ctgggttcca g                                      21

<210> SEQ ID NO 23
<211> LENGTH: 21
<212> TYPE: DNA
<213> ORGANISM: Mus musculus

<400> SEQUENCE: 23
attwtcagct tcctgctaat c                                      21
```

<210> SEQ ID NO 24
<211> LENGTH: 21
<212> TYPE: DNA
<213> ORGANISM: Mus musculus

<400> SEQUENCE: 24
ttttgctttt ctggattyca g                                              21

<210> SEQ ID NO 25
<211> LENGTH: 21
<212> TYPE: DNA
<213> ORGANISM: Mus musculus

<400> SEQUENCE: 25
tcgtgttkct stggttgtct g                                              21

<210> SEQ ID NO 26
<211> LENGTH: 20
<212> TYPE: DNA
<213> ORGANISM: Mus musculus

<400> SEQUENCE: 26
atggaatcac agrcycwggt                                                20

<210> SEQ ID NO 27
<211> LENGTH: 21
<212> TYPE: DNA
<213> ORGANISM: Mus musculus

<400> SEQUENCE: 27
tcttgttgct ctggttycca g                                              21

<210> SEQ ID NO 28
<211> LENGTH: 24
<212> TYPE: DNA
<213> ORGANISM: Mus musculus

<400> SEQUENCE: 28
cagttcctgg ggctcttgtt gttc                                           24

<210> SEQ ID NO 29
<211> LENGTH: 19
<212> TYPE: DNA
<213> ORGANISM: Mus musculus

<400> SEQUENCE: 29
ctcactagct cttctcctc                                                 19

<210> SEQ ID NO 30
<211> LENGTH: 24
<212> TYPE: DNA
<213> ORGANISM: Mus musculus

<400> SEQUENCE: 30
gatggtggga agatggatac agtt                                           24

<210> SEQ ID NO 31
<211> LENGTH: 24
<212> TYPE: DNA
<213> ORGANISM: Mus musculus

<400> SEQUENCE: 31

-continued

```
gayattgtgm tsacmcarwc tmca                                          24

<210> SEQ ID NO 32
<211> LENGTH: 21
<212> TYPE: DNA
<213> ORGANISM: Mus musculus

<400> SEQUENCE: 32
cgtttgattt ccagcttggt g                                             21

<210> SEQ ID NO 33
<211> LENGTH: 21
<212> TYPE: DNA
<213> ORGANISM: Mus musculus

<400> SEQUENCE: 33
cgttttattt ccagcttggt c                                             21

<210> SEQ ID NO 34
<211> LENGTH: 21
<212> TYPE: DNA
<213> ORGANISM: Mus musculus

<400> SEQUENCE: 34
cgttttattt ccaactttgt c                                             21

<210> SEQ ID NO 35
<211> LENGTH: 21
<212> TYPE: DNA
<213> ORGANISM: Mus musculus

<400> SEQUENCE: 35
cgtttcagct ccagcttggt c                                             21
```